US011147990B2

(12) United States Patent
Burdette

(10) Patent No.: US 11,147,990 B2
(45) Date of Patent: Oct. 19, 2021

(54) ULTRASOUND THERAPY CATHETER WITH MULTI-CHAMBERED BALLOONS FOR TRANSLUMINAL LONGITUDINAL POSITIONING

(71) Applicant: Acoustic MedSystems, Inc., Savoy, IL (US)

(72) Inventor: Everette C. Burdette, Savoy, IL (US)

(73) Assignee: ACOUSTIC MEDSYSTEMS, INC., Savoy, IL (US)

( * ) Notice: Subject to any disclaimer, the term of this patent is extended or adjusted under 35 U.S.C. 154(b) by 1128 days.

(21) Appl. No.: 14/775,366

(22) PCT Filed: Mar. 12, 2014

(86) PCT No.: PCT/US2014/024938
§ 371 (c)(1),
(2) Date: Sep. 11, 2015

(87) PCT Pub. No.: WO2014/165242
PCT Pub. Date: Oct. 9, 2014

(65) Prior Publication Data
US 2016/0030773 A1 Feb. 4, 2016

Related U.S. Application Data

(60) Provisional application No. 61/778,063, filed on Mar. 12, 2013.

(51) Int. Cl.
A61N 7/02 (2006.01)
A61B 8/08 (2006.01)
(Continued)

(52) U.S. Cl.
CPC ............... *A61N 7/022* (2013.01); *A61B 8/085* (2013.01); *A61B 8/12* (2013.01); *A61B 8/445* (2013.01);
(Continued)

(58) Field of Classification Search
CPC ............ A61B 34/20; A61B 2090/3484; A61B 2018/00791; A61B 2018/00577;
(Continued)

(56) References Cited

U.S. PATENT DOCUMENTS 4,276,874 A * 7/1981 Wolvek ............. A61M 25/0054
600/18
5,921,978 A * 7/1999 Thompson ........ A61M 25/0108
604/523

(Continued)

FOREIGN PATENT DOCUMENTS

EP 2 455 133 5/2012

OTHER PUBLICATIONS

Non-Final Office Action in U.S. Appl. No. 14/765,765, dated Mar. 6, 2017, 9 pages.
(Continued)

*Primary Examiner* — Keith M Raymond
*Assistant Examiner* — Patrick M Mehl
(74) *Attorney, Agent, or Firm* — Foley & Lardner LLP

(57) ABSTRACT

A multi-angular ultrasound device. Multi-angular ablation patterns are achieved by a catheter based ultrasound transducer having a plurality of transducer zones. A multi-chambered balloon is positioned on the catheter.

20 Claims, 42 Drawing Sheets

(51) Int. Cl.
*A61B 8/12* (2006.01)
*A61B 8/00* (2006.01)
*A61N 7/00* (2006.01)
A61B 18/00 (2006.01)
A61B 90/00 (2016.01)

(52) U.S. Cl.
CPC ........... *A61B 2018/00023* (2013.01); *A61B 2018/00517* (2013.01); *A61B 2018/00523* (2013.01); *A61B 2018/00791* (2013.01); *A61B 2090/378* (2016.02); *A61N 2007/0043* (2013.01); *A61N 2007/027* (2013.01)

(58) Field of Classification Search
CPC .... A61B 2090/378; A61B 2018/00523; A61B 2018/00023; A61B 18/00791; A61B 2018/00517; A61B 8/445; A61B 2017/22051; A61B 2017/22048; A61B 2017/3486; B06B 1/0625; A61N 2007/0043; A61J 15/0049; A61M 25/10
See application file for complete search history.

(56) References Cited

U.S. PATENT DOCUMENTS

| | | | | |
|---|---|---|---|---|
| 6,540,655 | B1* | 4/2003 | Chin | A61N 5/1001 600/3 |
| 6,796,960 | B2* | 9/2004 | Cioanta | A61B 18/04 604/103.01 |
| 7,476,235 | B2* | 1/2009 | Diederich | A61M 25/10 606/192 |
| 2003/0120208 | A1* | 6/2003 | Houser | A61M 25/104 604/103.04 |
| 2003/0139790 | A1* | 7/2003 | Ingle | A61B 18/1482 607/99 |
| 2004/0082859 | A1* | 4/2004 | Schaer | A61B 18/18 600/459 |
| 2005/0234343 | A1* | 10/2005 | Maschke | A61B 8/12 600/467 |
| 2006/0206105 | A1* | 9/2006 | Chopra | A61B 5/055 606/27 |
| 2007/0129749 | A1* | 6/2007 | Thomas | A61M 25/10 606/194 |
| 2007/0255267 | A1* | 11/2007 | Diederich | A61N 7/022 606/27 |
| 2010/0049186 | A1 | 2/2010 | Ingle et al. | |
| 2012/0296240 | A1 | 11/2012 | Azhari | |
| 2016/0008635 | A1 | 1/2016 | Burdette et al. | |

OTHER PUBLICATIONS

Final Office Action in U.S. Appl. No. 14/765,765, dated Sep. 7, 2017, 12 pages.
International Search Report and Written Opinion for Application No. PCT/US2014/014728, dated Jun. 5, 2014, 6 pages.
International Search Report and Written Opinion for Application No. PCT/US2014/024938, dated Aug. 21, 2014, 7 pages.
Non-Final Office Action in U.S. Appl. No. 14/765,765, dated Jul. 24, 2018, 13 pages.
Chen, X., et al., "Optimisation-based thermal treatment planning for catheter-based ultrasound hyperthermia," International Journal of Hyperthermia, Feb. 2010, 26(1):39-55.
Final Office Action in U.S. Appl. No. 14/765,765, dated Jan. 25, 2019, 20 pages.

* cited by examiner

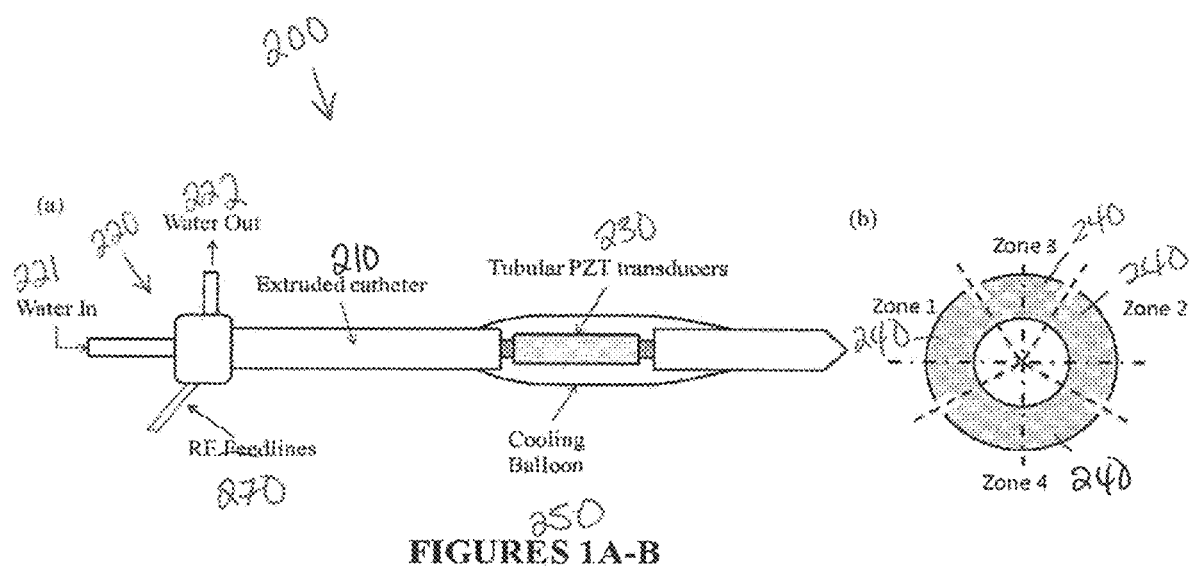
FIGURES 1A-B

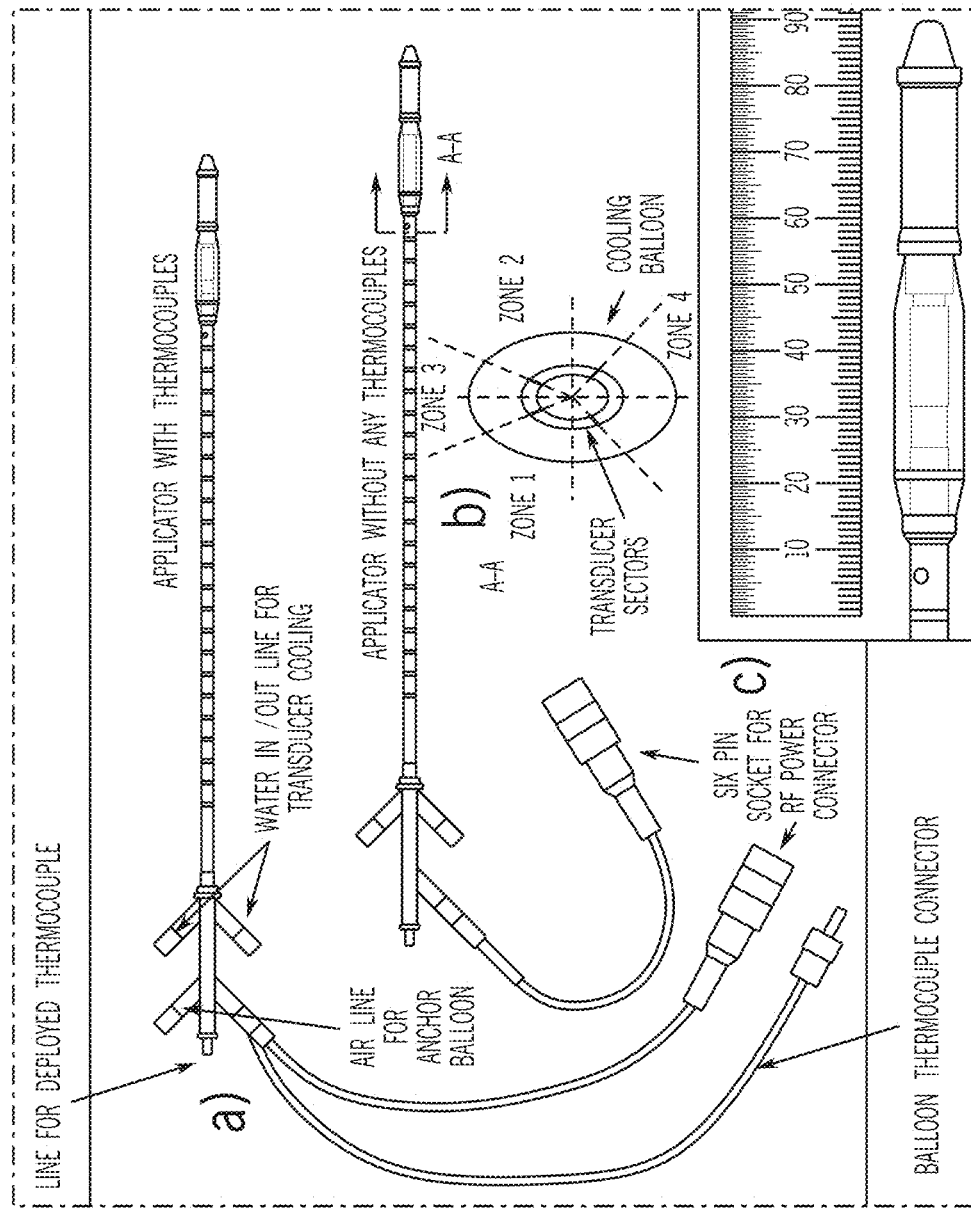
FIG. 2A-C

FIGURES 27A-B

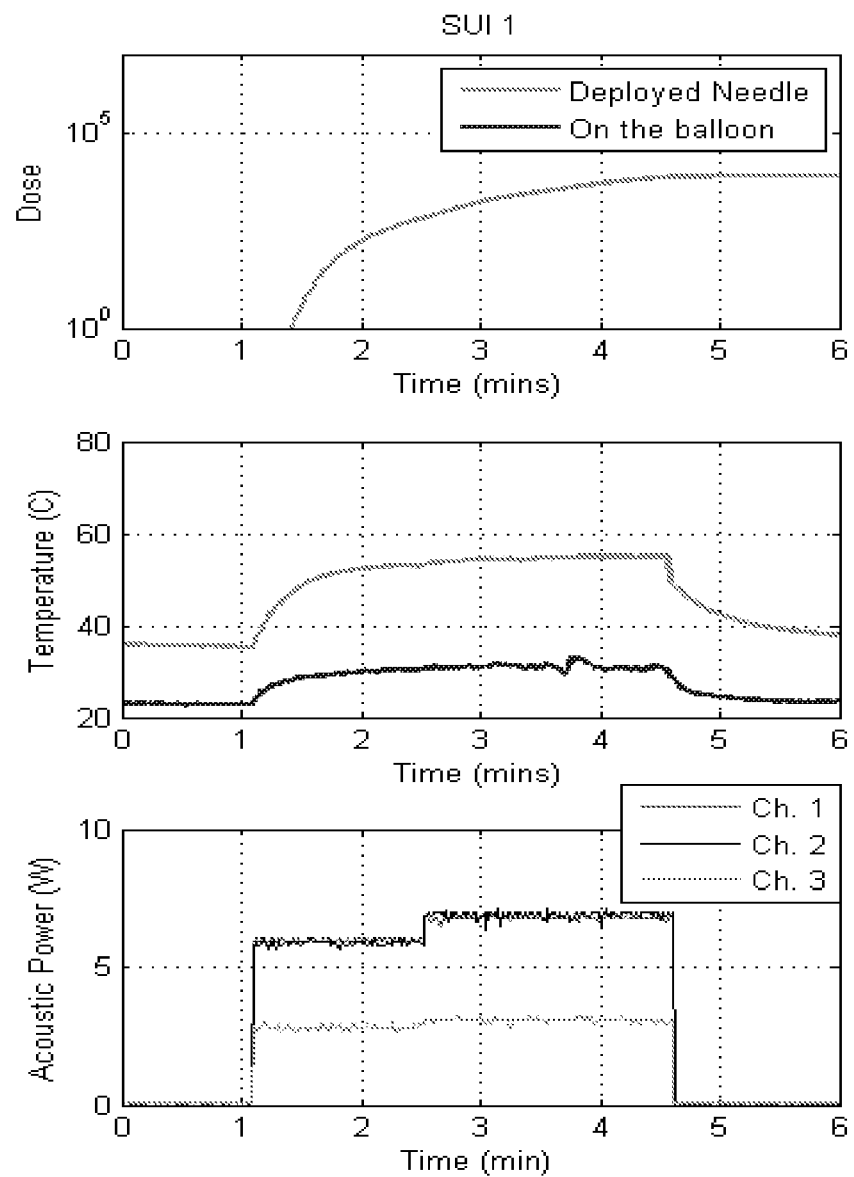
FIGURES 29A-C

ULTRASOUND THERAPY CATHETER WITH MULTI-CHAMBERED BALLOONS FOR TRANSLUMINAL LONGITUDINAL POSITIONING

CROSS REFERENCE TO RELATED APPLICATIONS

This application is a National Stage of International Application No. PCT/US2014/024938, filed Mar. 12, 2014, which claims priority to U.S. Application No. 61/778,063 filed Mar. 12, 2013, which both are incorporated herein by reference in their entirety.

STATEMENT OF GOVERNMENT INTEREST

Some work described herein supported by the National Cancer Institute (National Institutes of Health, Bethesda, Md.) under NIH Grant R44CA134169 and Grant R44CA112852. The United States Government may have certain rights in inventions described herein.

FIELD OF THE INVENTION

The present invention generally relates ultrasound treatment, specifically ultrasound thermal therapy.

BACKGROUND OF THE INVENTION

Thermal therapy has been widely investigated as an alternative to surgical procedures for treatment of diseased tissue. Minimally invasive catheter based high-intensity ultrasound has been investigated in depth by a few groups for treatment of diseased tissue. Such technology has the benefit of targeting the treatment location accurately with the least minimal invasive procedure. Moreover, large ablation tissue volumes can be achieved with single insertion. The applicability of such technology improves drastically with the capability of accurately producing multi-angular ablation patterns. Multi-angular ablation patterns can be produced to result in treating the diseased tissue without damaging the nearby healthy tissue.

Researchers have investigated the use of single direction element transurethral ultrasound applicator to treat prostate cancer and ablated the prostate by rotating the applicator. By using tubular transducers, such ablation can be produced without rotating the applicator. By exciting different sectors with different frequency and power in a multi-sectored tubular ultrasound transducer, many distinct beam patterns can be obtained. Designing different geometries of the sectored transducer can produce various ablation patterns. The frequency of the element and the input power can be used to change the depth of penetration of the ultrasound wave into the tissue and thus control the ablated tissue volume. Computational modeling can provide optimized design parameters to design multi-sectored tubular transducers efficiently for specific ablation pattern. Previous studies have shown good agreement between experimental and simulation results obtained from finite element analysis of bio-heat equation.

Among the many types of disorders and diseases that have been investigated for possible treatment by ultrasound, Stress urinary incontinence (SUI) is one of the most common. SUI is the most common type of urinary incontinence symptomatic in 15 million adult women in the US. Risk factors for SUI include advancing age, childbirth, smoking and obesity. Conditions that cause chronic coughing, such as chronic bronchitis and asthma, may also increase the risk and/or severity of symptoms of stress incontinence. SUI is defined by the International Continence Society as "leakage on effort, exertion, sneezing, or coughing". In normal condition, the endopelvic fascia provides support to the female urethra. Typically, damage to this structure (e.g., childbirth) weakens that support, rendering the urethra and sphincter less able to resist normal pelvic forces, allowing the urethra to distend and urine leakage.

Treatment options range from pharmaceuticals, surgical procedures, and thermal therapies. Pharmaceuticals are the primary physician directed treatment, representing $1.2 billion in annual expenditures in 2005. Pharmaceuticals and pads do not provide permanent relief, but impose a constant economic drain with undesirable physical and quality of life side-effects. Injecting bulking agents to treat SUI showed both objective and subjective improvements. Presently, the synthetic midurethral sling, inserted via a retropubic or transobturator is the defecto gold standard for surgical treatment of SUI. In these procedures, a sheet of material is placed between the urethra and vagina, and attached at both ends to the pubis. This "sling" or "hammock" effectively replicates tightening of the endopelvic fascia, pulling the urethra in a superior/posterior direction, and increasing the hydrostatic pressure required to void the bladder. Other techniques include suturing the bladder neck to the back of the pubic bone. The Burch procedure can be performed via laparoscopy with robot assistance. Synthetic midurethral sling procedures are widely performed for treatment of female SUI, which is a simple and quick procedure with low morbidity. The surgical procedures are an effective treatment option, with 90% improvement rates. However, the surgical interventions require a hospital setting with significant anesthetic intervention (typically general), as well as incisions in the vagina or the suprapubic region. Failure rates are reported in the 5% to 10% range and consist primarily of bladder perforation, immediate post-procedure retention, infection, and de novo incontinence at some period post procedure.

The application of RF thermal therapy, similar to the approach commonly used in orthopedic medicine to tighten joint capsules, has been investigated as a surgical technique with a direct application of RF energy and heat to tighten and remodel the endopelvic fascia. This surgical technique requires two 2 cm incisions within the superior/lateral aspects of the vagina to expose the endopelvic fascia to RF heating. This thermal shrinkage of the endopelvic fascia has demonstrated long term improvement rates at greater than 75%. In another study researchers showed shrinkage of endopelvic fascia (25-50%) upon RF treatment of SUI, and observed that the tissue does not re-stretch during the healing time. The underlying science of this approach is sound as temperature elevation (55-70 C, 1-3 minutes) shrinks the collagen by affecting the basic structure of the molecule. Wall and others have confirmed that thermal remodeling of collagen does occur in different time intervals in relation to elevated temperatures. Further, the thermal insult stimulates the generation of new collagen, or neocollagenesis, to further strengthening and restore the collagenous tissues. This is the basis for using heat for ligament tightening, joint stability, and skin tightening. Minimally invasive devices, utilizing transurethral delivered RF energy to the bladder neck region for RF remodeling of the endopelvic fascia, have been inconsistent because the physics of RF ablation (including tissue resistivity variability) do not provide consistent predictable application of therapeutic levels of energy at levels as deep as 10 mm and without causing injury to the urethra, bladder neck, or vagina.

All current surgical interventions involve incisions or needle insertions through the urethral wall or vaginal wall, in some instances depositing or placing implants. RF ablation have has shown to alter connective tissue and damage muscle in joint capsule and preserves the synovium from damage with regeneration of synovium after 7 days of surgery. Lopez et al., observed that RF energy altered intermolecular interaction between collagen molecules (alpha chains) resulting into molecular disorganization due to thermal energy effect. In another study researchers showed shrinkage of endopelvic fascia upon RF treatment of SUI. Regeneration of normal tissue was confirmed in two 6-month patient follow-up from histological analysis. RF treatment remodeled porcine bladder neck and proximal urethra from histopathological analysis after 8 weeks of survival study. The SURx RFA device treated endopelvic collagen to maximum temperature of 80° C. with significant reduction of incontinence; it did not succeed in marketplace because it was invasive requiring a surgical procedure (insertion of strips along fascia 1 cm lateral and 2 mm deep for entire length of urethra) and less effective than a hammock sling. The Renessa device required the insertion of needles at multiple locations (36 discrete points) primarily treating near the bladder neck. Results were inadequate to gain market adoption. Loss of urethral pressure from the surrounding supporting tissues results in SUI. Urethral support has been determined to be greatest in the mid-region.

The potential of thermal therapy for shrinking and tightening the endopelvic fascia as a possible treatment methodology for SUI has been clearly demonstrated; however, there is a clear need for minimally-invasive application of heating energy versus surgical approaches, and better more sophisticated and selective approaches of targeting the endopelvic fascia from within the urethra are required.

SUMMARY OF THE INVENTION

One embodiment of the invention relates to Multi-zoned tubular ultrasonic transducer arrays. One embodiment relates to methods of using these transducer configurations to achieve a multi-angular directional ablation pattern.

Additional features, advantages; and embodiments of the present disclosure may be set forth from consideration of the following detailed description, drawings, and claims. Moreover, it is to be understood that both the foregoing summary of the present disclosure and the following detailed description are exemplary and intended to provide further explanation without further limiting the scope of the present disclosure claimed.

BRIEF DESCRIPTION OF THE DRAWINGS

The foregoing and other objects, aspects, features, and advantages of the disclosure will become more apparent and better understood by referring to the following description taken in conjunction with the accompanying drawings, in which:

FIG. 1A is a schematic of a flexible catheter based ultrasound applicator,

FIG. 1B is a cross-sectional view of a multi-sectored array tubular ultrasonic transducer.

FIG. 2A illustrates an applicator with thermocouples; FIG. 2B illustrates an applicator without thermocouples, and FIG. 2C illustrates a cross-section along A-A of FIG. 2B.

FIG. 3A illustrates a close-up of the transurethral cooling balloon and the bladder balloon; FIG. 3B illustrates a close-up of the transducer within the transurethral balloon.

FIGS. 29A-C (a) dose delivered to the tissue at both the thermocouple locations, (b) Temperature profile of the deployed thermocouple and the thermocouple on the balloon, and (c) delivered acoustic power by all the RF channels for EWE-99 SUI2. Note that no dose was delivered at the balloon surface (i.e. at the urethral wall).

DETAILED DESCRIPTION OF THE PREFERRED EMBODIMENTS

Figures 3A, 3B:
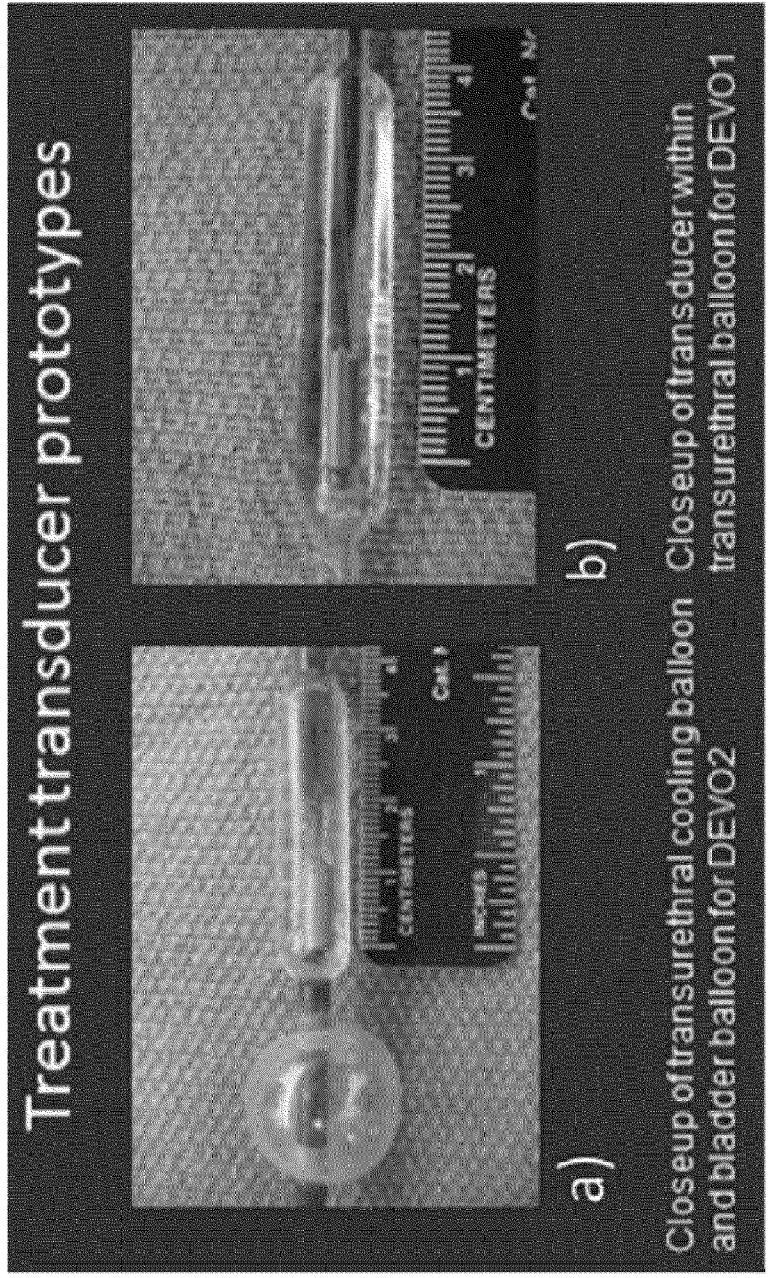
FIGS. 3A-B shows a bi-sectored tubular array applicators, one with bladder anchor balloon.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and made part of this disclosure.

Catheter based ultrasound ablation devices provide a minimally invasive procedure for thermal therapy. However, the success of such procedures depends on accurately delivering the thermal dose to the tissue. One of the main challenges of such therapy is to deliver thermal therapy at the target location without damaging the surrounding tissue or major vessels and veins. To achieve such multi-directional capability, a multi-angular beam pattern is required.

1. Multi-Sectored Ultrasonic Device

One aspect of the invention relates to a multi-sectored tubular ultrasonic transducer and control the directionality of the acoustic power delivered to the tissue by each sector simultaneously. Multi-zoned tubular ultrasonic transducer arrays with three active sectors were constructed for proof of concept. Using these transducer configurations, a multi-angular ablation pattern was created in ex vivo chicken breast tissue as described in the Example section.

FIG. 1A illustrates a multi-sectored ultrasonic device 200. The device 200 has a catheter body 210 (an embodiment of which is shown as an extruded structure in FIG. 3). A cooling mechanism 220 is provided. For example, as illustrated, the catheter body 210 includes, as part of the cooling mechanism 220 a water inlet 221 and a water outlet 222. Cables such as RF feedlines or power supply lines 270 are included and may pass through the body 210, such as to the transducers 230. One or more transducers 230 are disposed about the catheter body 210. The one or more transducers may be multi-sectored. In one embodiment each sector 240 can be separately powered, such as by a separate wire back to a common power source. FIG. 1B illustrates a cross-sectional view of the zones defined by the ultrasound emitted from four zones. In one embodiment, the one or more transducers may be sectored into zones radially and longitudinally in addition to radially as shown in FIG. 1B.

In one embodiment, single element tubular transducers, such as piezoelectric devices, including but not limited to ceramic perovskites such as lead zirconium titanate (PZT), are used to manufacture the flexible catheter based ultrasound applicator as shown in FIG. 1A. The transducer was mounted on a mandril and attached to the extruded catheter. The transducer was 1.0-1.5 cm long, with control of heating energy in the angular expanse. A coupling balloon was used to cool the transducer and balloon material was chosen to exhibit minimal attenuation of the ultrasound wave propagating through it. The flexible multi-lumen delivery catheter had channels for powering devices and circulating cooling flow within the cooling balloon. The diameter of the cooling balloon was 7 mm. In one embodiment, the multi-angular sectored design allows a single tubular transducer, to be sub-divided, not mechanically, but electrically, to produce different active sub-elements each with its own angle of ultrasound power output signal radiation. Further, these transducers may be "stacked" end-to-end to provide differential control along the length of the catheter in addition to angularly circumferentially around the transducer.

The device designs relate to sectored tubular array devices. As noted above, planar and focused devices were built and tested, in addition to a bi-sectored tubular design. The bi-sectored tubular design was expanded to three angular sectors based on computer simulations and ex-vivo (chicken) tissue test results described below. Two examples of the bi-sectored array applicators with acoustic coupling—cooling balloons are shown in FIGS. 2A-B.

Ten of the catheters, each having with two different angular sectors circumferentially around a single transducer of fixed longitudinal dimension—typically 1 cm to 1.5 cm long, were fabricated for animal model development experiments. For the animal studies described below, the catheters are dual sectored array catheter of a 70-80° design.

Figure 4:
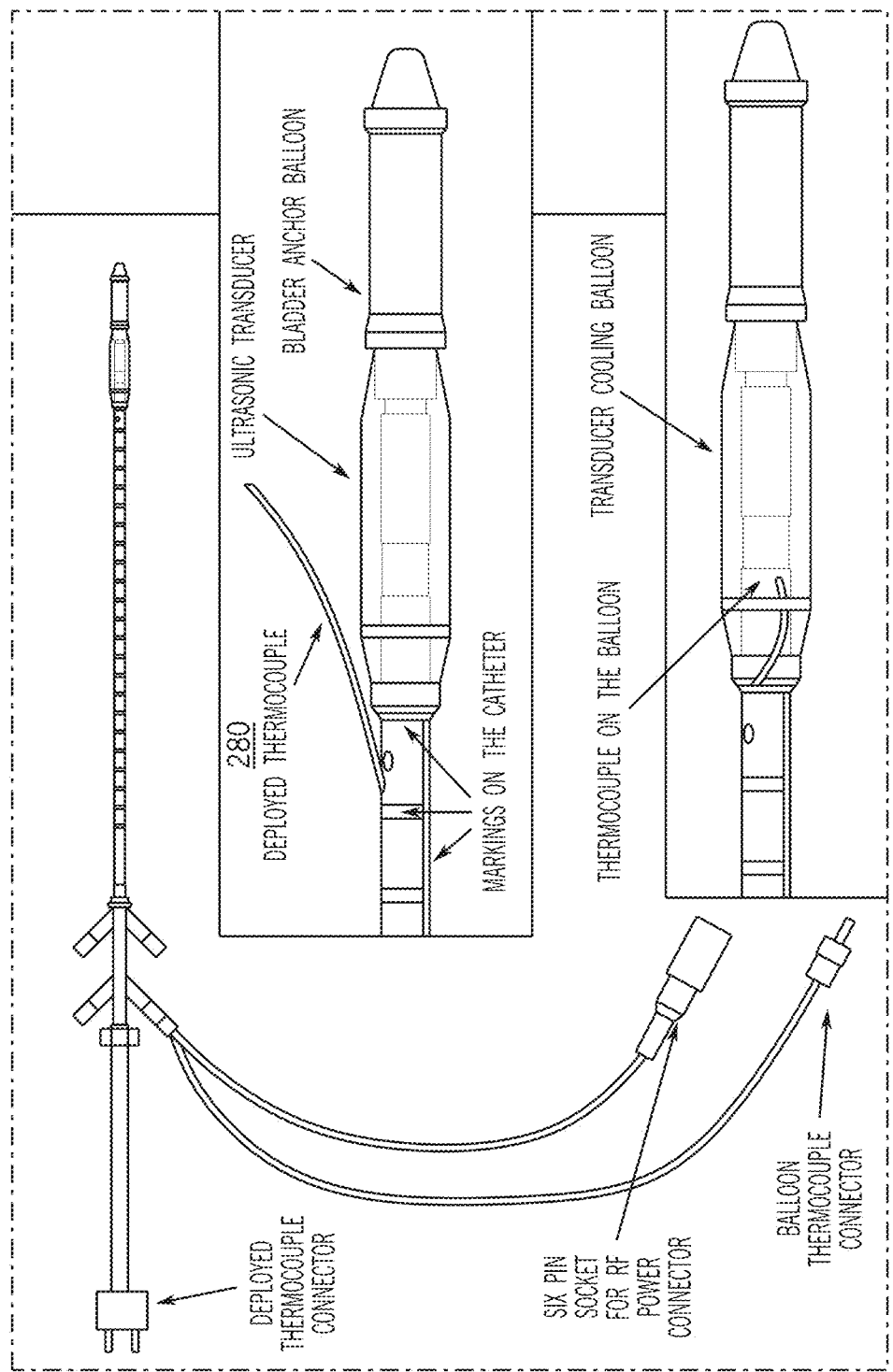
FIG. 4 is an ultrasound ablation applicator, thermocouple on the balloon and the deployed thermocouple position on the applicator. The anchor balloon for deployment in the bladder is shown at the far right in this figure.

In one embodiment, the applicator may have either bi-sectored arrays or tri-sectored arrays. FIG. 4 illustrates one embodiment of an applicator. Results of electrical performance and applicator efficiency are described further below.

In certain embodiments, such as illustrated in FIG. 4, the applicator may be manufactured with different size holes through an extruded solid tube (cross-section of extruded portion shown in FIG. 3). The diameter of each extruded hole depends on the purpose such as depending on the electrical wire diameter used for connecting the RF generator the holes. The extruded tube is different in that it is integral to the assembly, whereas the other method we use to manufacture requires mounting of the transducer within a segment of the catheter.

As shown in FIG. 1A, a cooling balloon 250 may be provided to cool the tissue exposed to the one or more transducers 230. The cooling balloon 250 may be operated by an airline or water line. As discussed further below, a bladder balloon 260 may be disposed adjacent the end of the catheter 210 to control the bladder volume and or to provide cooling or other changes to the bladder or other tissue located distal from the catheter's transducers 230.

In one embodiment, for example as shown in FIG. 4, the device includes a temperature sensor 280 such as a thermocouple to measure temperature profile in the treatment zone so that actual dose delivered to the tissue during the treatment real-time will be monitored. In one particular embodiment, the temperature sensor is a thermocouple on the transducer cooling balloon that can monitor the temperature profile, for example, of the urethra wall during a treatment. In a further embodiment, a second temperature sensor (such as a thermocouple) was attached to the catheter such that it can be deployed to place in the treatment region during the treatment. The capability to deploy a preformed nitinol needle thermal sensor in one embodiment of an applicator is shown in FIG. 4.

Degassed water was circulated through the catheter for cooling the transducer during ablation. Degassed water was used to minimize the presence of bubbles. Transducers with four sectors as shown in FIG. 1C were used for the experiments. Out of the four sectors, three sectors were active for the experiments. Specifically zones 1, 2 and 3 were the active zones. The design allows the use of four sectors when required, and can be extended to a greater or fewer number as required. Three sectors were activated for the present study to demonstrate the significant advantage of localization and directional ablation produced with this technology.

Using electrical impedance and radiation force balance measurements, the center frequency and efficiency of each transducer element was estimated. The center frequency of each individual element was used to excite the respective element to maximize energy output. Continuous wave mode was used to excite the transducers. Typically transducer center frequency ranged from 6.5-7.5 MHz with acoustic efficiency of 50-60%.

Figure 5:
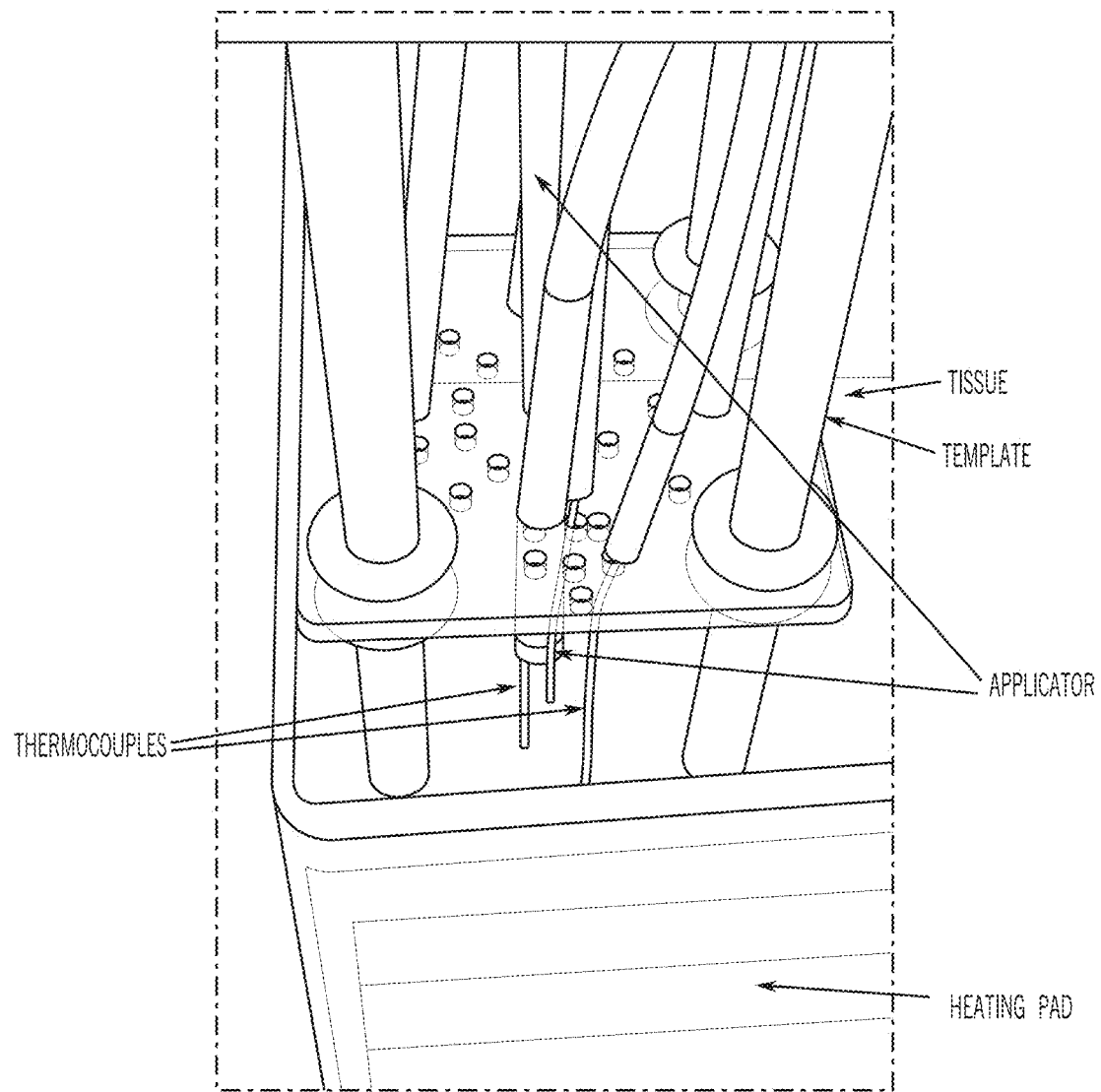
FIG. 5 shows the placement of thermocouples and the ultrasound applicator using the custom template. Sensors were inserted in tissue in both active zone directions and at inactive zones with respect to angular direction.

In one embodiment, needle thermocouples of typeT (Physitemp, N.J., USA) were used for monitoring temperature. Each needle was 100±2 mm long and 0.82 mm in diameter with 0.1° C. accuracy in temperature measurement with a 0.05 sec time constant. Thermocouples were placed at different distances from the ultrasound applicator and dose was calculated for each thermal sensor. A custom template was used to insert the applicator and thermocouples as shown in FIG. 5. The template helped in registering the location of each thermocouple with respect to the ultrasound applicator precisely. The temperature from each thermocouple was recorded at every 1 second. The thermal dose calculated from the thermocouple temperature-time profile is given by:

$$t_{43} = \sum_{t=0}^{t=final} R^{(43-T_t)} \Delta t, \begin{cases} R \equiv 0.25 \text{ for } T < 43° \text{ C.} \\ R \equiv 0.30 \text{ for } T \geq 43° \text{ C.} \end{cases} \quad (1)$$

where $T_t$ is the average temperature recorded by the thermocouple during time Δt. The unit of thermal dose is equivalent minutes at 43° C. Typically thermal dose of 240 equivalent minutes at 43° C. can produce necrosis in soft tissue.

Figure 10A:
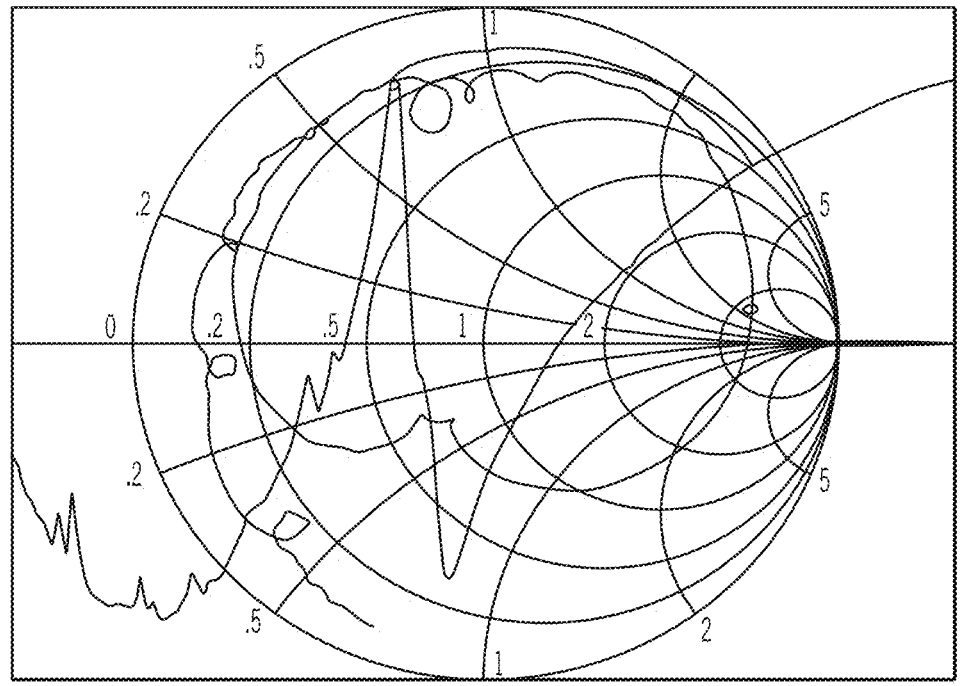
FIGS. 10A-C Smith chart of transducer impedance measurements for the latest applicator design specifically for 10(a) sector 1, 10(b) sector 2 and 10(c) sector 3. The table shows the power measurement conducted to determine the efficiency of each sector.
Figure 10B:
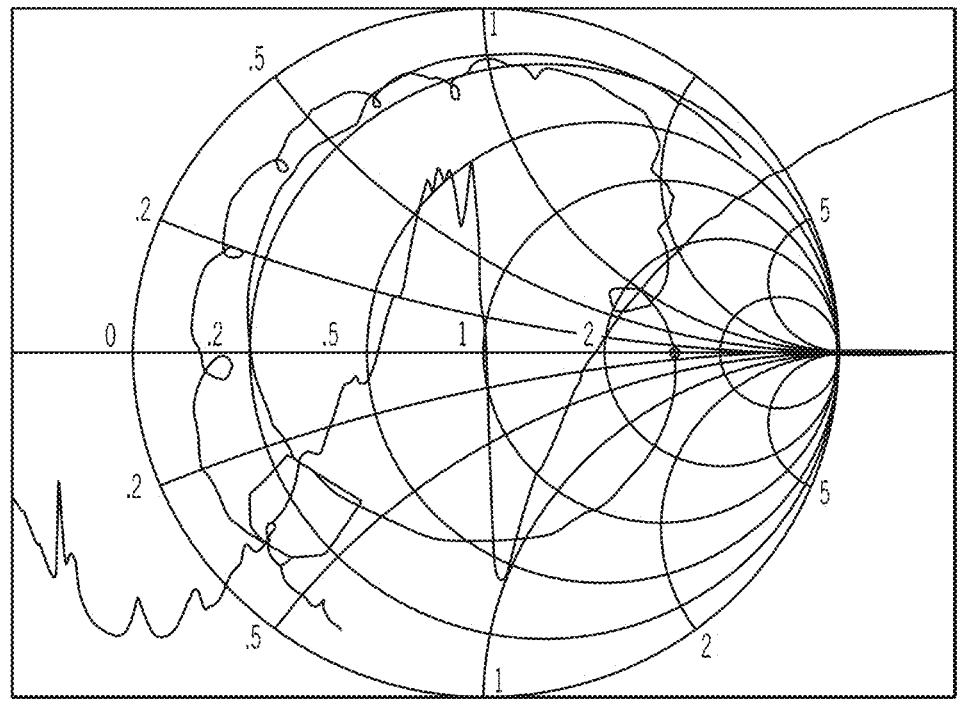
Figure 10C:
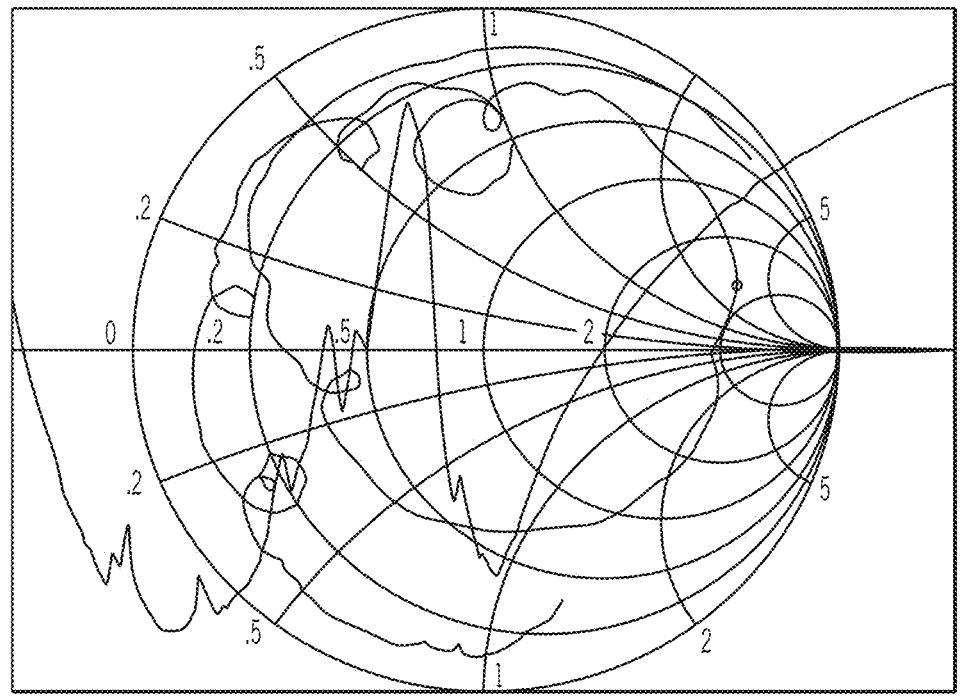

Efficiency of the electrical to acoustic power of the ablation catheters was measured using a pressure force-balance measurement system. An example Smith Chart used for impedance analysis for a three sectored applicator is shown in FIGS. 10A-C. The conversion efficiency for the ablation catheters from electrical input to ultrasound output ranged from 55% to 60%, with current designs yielding>50%. An efficiency of 50% is considered to be excellent.

Experiments were performed where the applicator was submerged into a water bath and held near the water surface to visualize the acoustic pressure wave pattern generated by the output acoustic power from the applicator. The results are shown in FIGS. 8A-F, where different sectors were excited to observe different patterns. Insonating a single sector at 6 W viewed longitudinally demonstrates a distinct collimated pattern of the ultrasound field of the sector was observed as shown in FIG. 8(b).

a. Ex Vivo Chicken Study

The purpose of the present study was to investigate the ablation pattern obtained using a multi-sectored tubular ultrasonic transducer. Experiments were conducted by activating two and three zones separately to investigate the ablation pattern of each case. The treatment was monitored by inserting several needle thermocouples into the tissue at various distances from the ultrasound applicator. The dose distribution was determined from the temperature-time profile recorded by each of the thermocouples. The multi-angular ablation pattern created by the transducer was compared with simulations based on the same design parameters. The simulations were performed by solving the bio-heat equation using finite element method. The experimental and simulation results are compared with respect to temperature and dose profiles. It was observed through visual inspection that one embodiment of the multi-sectored transducer could ablate a specific tissue region or multiple regions selectively while not damaging the desired surrounding tissue. Simulations results were presented by solving the Penne bio-heat equation using finite element method. The simulation results were compared with ex vivo results with respect to temperature and dose distribution in the tissue. Thermocouples located at 15 mm radially from the applicator indicated a peak temperature of greater than 52-55° C. and thermal dose of $10^3$-$10^4$ EQ mins at 43° C. Good agreement between experimental and simulation results was obtained.

i. Ultrasound Ablation Ex Vivo Chicken Study

Freshly excised ex vivo chicken breast muscle tissue was ablated using the flexible catheter based multi-directional ultrasound applicator. A custom template to hold the applicator and thermocouples, and a custom designed tissue holder was used in the experiment as shown in FIG. 5. The custom tissue holder had heating pads to maintain the tissue temperature at 35-37° C. The tissue was pre-heated to 37° C. using a temperature controlled water bath immediately prior and placed into the custom tissue holder for the ablation experiment.

Figure 26:
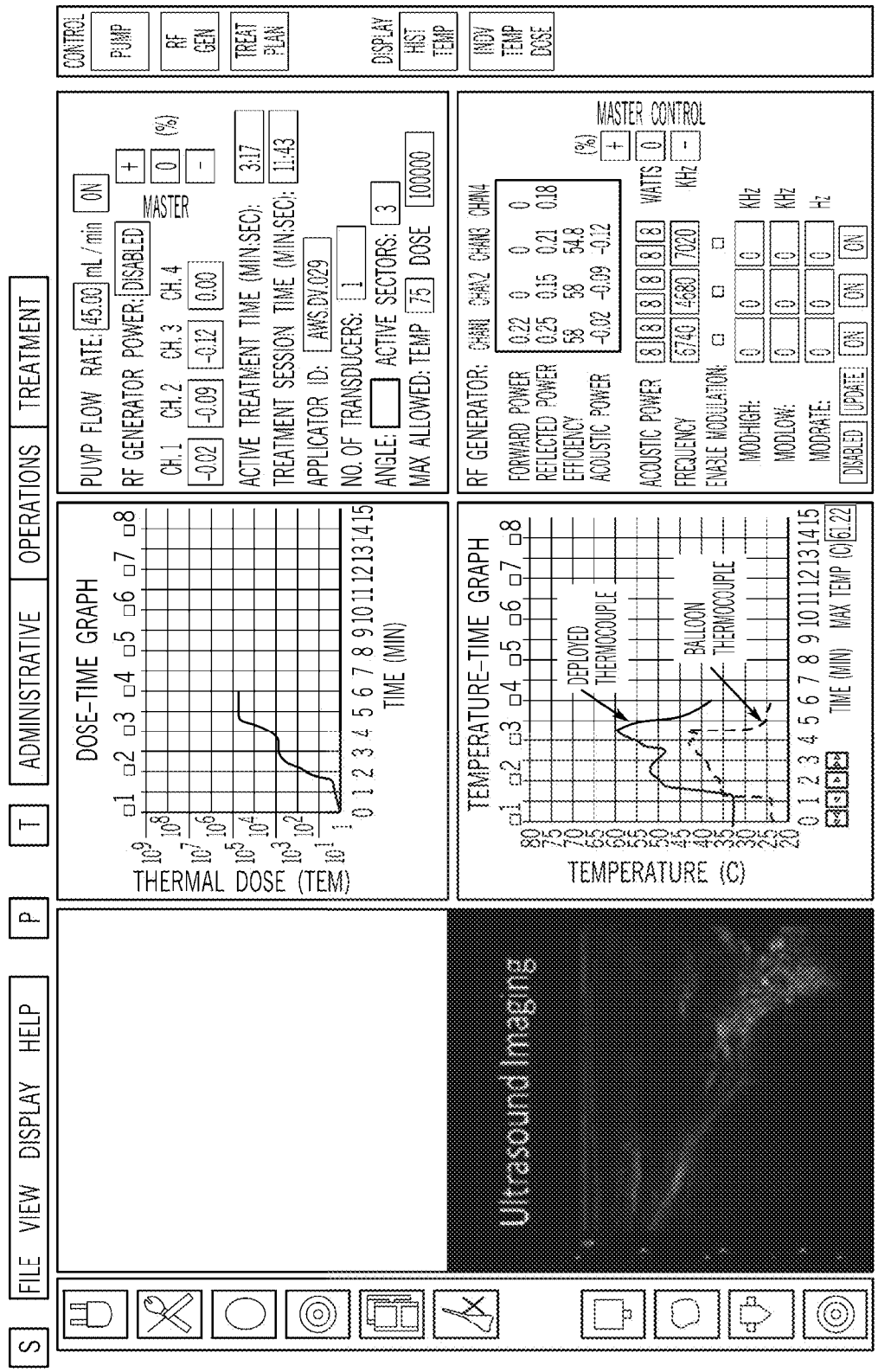
FIG. 26 An example treatment screen shot from ablation treatment software.

A software architecture for treatment planning, control, and monitoring was developed to communicate with the RF generator, water pump and the thermocouples using a user friendly graphical user interface. A screen-shot of the application software is shown in FIG. 26. The water pump was used to circulate degassed water through the cooling balloon. The left column of the screen shown in FIG. 26 was used for displaying the temperature and the dose versus time graphical information. The right column was used for displaying the controls and experimental treatment parameters used for the study experiments. The buttons at the right column edge of the screen were used for hardware control screens selection. The menu items at the top were used for administrative purposes such as patient management, file management and other tasks. The software has the functionality to create and execute treatment plans.

Typically 6-7 W (acoustic) was delivered to the tissue by the ultrasound applicator from zone 1 and 2. Acoustic power of 2-3 W was delivered to the tissue by the ultrasound applicator from zone 3. The lower power for zone 3 enabled to visualize the different ablation pattern intensity that could be achieved using the proposed technology. The acoustic wattage was estimated by considering the system efficiency, transducer efficiency and the transmission through the catheter to the tissue. Water flow rate of 40-50 ml/min was used for each treatment for cooling the ultrasound ablation transducers in the applicator.

Needle thermocouples were inserted at different distance from the applicator to monitor temperature profile during treatment. Thermocouples at 5 mm, 10 mm and 15 mm radially from the applicator in different zones were inserted using the custom template as shown in FIG. 5. The tip of each of the thermocouples was placed at the center of the ultrasonic transducer along the vertical axis. The thermocouples were denoted as Z1-10, Z2-5 etc. The notation for each thermocouple was as follows: Z1, Z2, Z3 and Z4 refer to the four different zones and the number that follows refers to the distance between the thermocouples and the applicator cooling balloon surface in the radial direction. For example Z1-5 refers to the thermocouple placed in zone 1 at 5 mm away from the cooling balloon. All the thermocouples were placed within the field of the ablation pattern for the respective active sectors.

ii. Finite Element Modeling

The finite modeling similar to known techniques (P. Prakash, V. A. Salgaonkar, E. C. Burdette, and C. J. Diederich, "Hepatic ablation with multiple interstitial ultrasound applicators: initial ex vivo and computational studies," in *Society of Photo-Optical Instrumentation Engineers (SPIE) Conference Series*, 2011, pp. 79010R-79010R) was used to simulate the bio-heat equation with appropriate boundary conditions. The heat transfer in tissue during ultrasound ablation was modeled using bio-heat equation given by:

$$\rho c \frac{\partial T}{\partial t} = \nabla \cdot k \nabla T + Q_S - \dot{m}_{b_l} c_{b_l} (T - T_{b_l}), \quad (2)$$

where ρ is the tissue density, r is the specific heat capacity, T is the temperature, k is the thermal conductivity, $Q_s$ is the acoustic power deposited, $\dot{m}_{bl}$ is the blood mass perfusion rate, $c_{bl}$ is the specific heat capacity of blood and $T_{bl}$ is the temperature of blood flow. For the current study the blood perfusion term was neglected since there was no blood flow in the ex vivo tissue. The acoustic power deposition term is given by:

$$Q_S = 2\alpha I_S \frac{r_0}{r} e^{-2\int \mu r' dr'}, \quad (3)$$

where α is the ultrasound absorption coefficient of the tissue, $I_s$ is the acoustic power intensity at the transducer face, $r_0$ is the radius of the transducer, r is the radial distance from the transducer surface, μ is the ultrasound attenuation coefficient and r' is the radial distance from the applicator surface. The values used for the various parameters are tabulate in Table 1.

TABLE 1

Nominal values for tissue properties used in FEM model of the bioheat equation.

| Parameter | Units | Value |
| --- | --- | --- |
| k (thermal conductivity) | W m$^{-1}$ K$^{-1}$ | 0.56 |
| c (specific heat capacity) | J kg$^{-1}$ K$^{-1}$ | 3639 |
| α (ultrasound absorption coefficient) | Np m$^{-1}$ MHz$^{-1}$ | 4.6 |
| μ (ultrasound attenuation coefficient) | Np m$^{-1}$ MHz$^{-1}$ | 4.6 |
| $r_0$ (transducer radius) | mm | 1.75 |

Commercial software COMSOL Multiphysics (COMSOL Inc., Burlington, Mass.) was used to simulate the bio-heat model using the finite element method (FEM). For all the simulations, the initial tissue temperature was set to 37° C. The boundary of the tissue was set to a fixed temperature of 37° C. A convective heat transfer boundary condition was applied on the inner catheter wall to simulate water cooling given by:

$$\vec{n}.k\nabla T = h(T_\infty - T), \quad (4)$$

where h=4500 W m$^{-1}$K$^{-1}$ is the convective heat transfer coefficient and $T_\infty$=20° C. is the temperature of the cooling water. An irregular FEM mesh consisting of quadratic Lagrangian elements was used to discretize the solution space. A sub-millimeter mesh resolution (maximum element edge length~0.5 mm) was employed at the applicator surface, with progressively increasing mesh element size away from the applicator. Maximum element edge length was restricted to 3 mm within the entire computational domain. A nonlinear, implicit solver with variable time steps (0.001<Δt<5 s) was used to solve the numerical problem. The three-dimensional temperature profile was determined using the FEM. Using the FEM results, contour plots of the temperature and dose profiles were constructed for visualizations.

iii. Results

Figure 8:
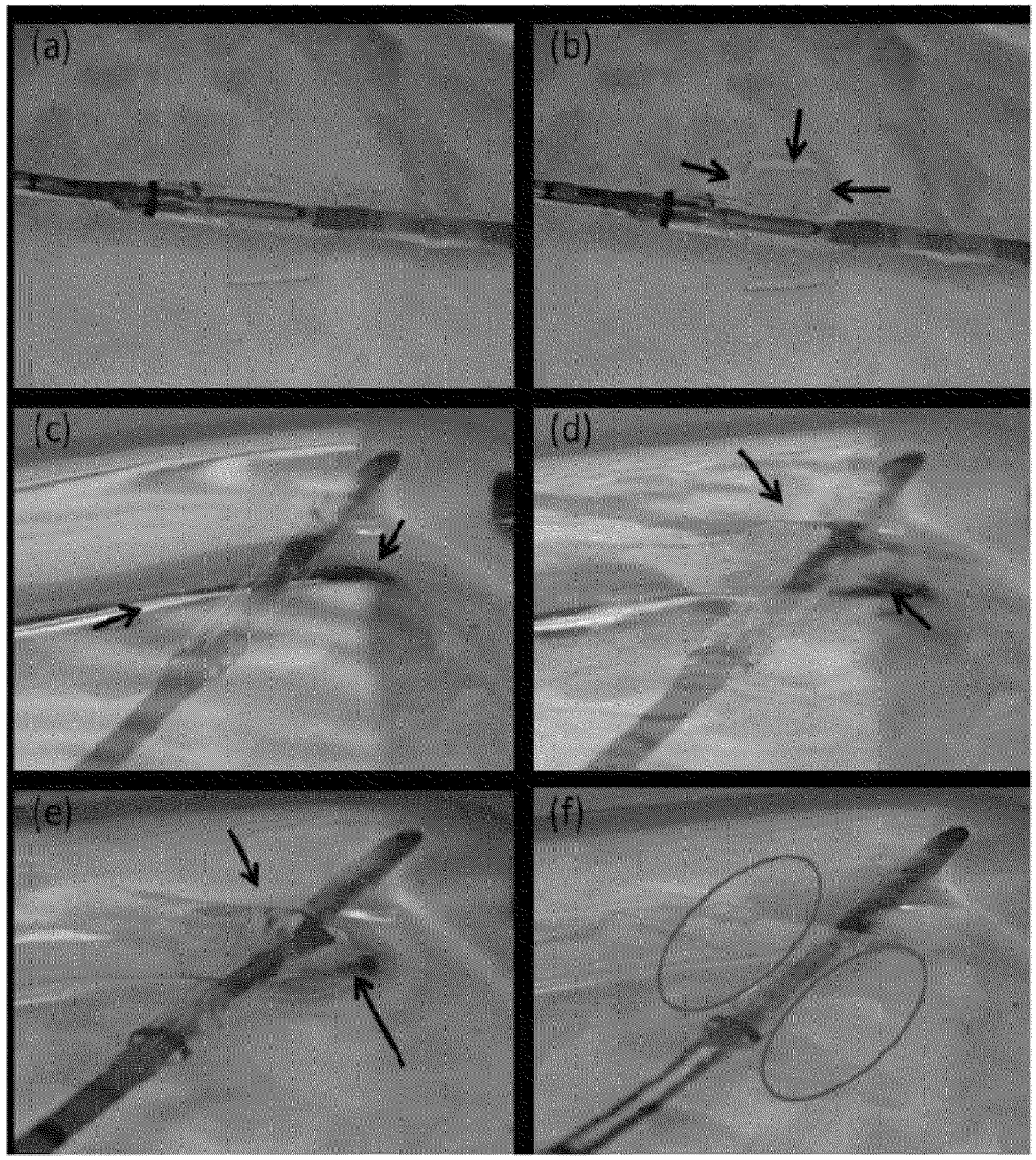
FIG. 8 shows the acoustic intensity wave pattern generated at the surface of the water bath for the given output acoustic power using (8A) 0 Watts (no power), (8B) 6 W for a lateral angular sector, (8C) 6 W for two lateral angular sectors, (8D) 6 W for all three angular sectors, (8E) 6 W for all three sectors rotated ~20 deg counterclockwise, and (8F) 6 W for two larger sectors. (The black arrows (b-e) and ovals (f) indicate the water wave pattern).

Experiments were performed where the applicator was submerged into a water bath and held near the water surface to visualize the acoustic pressure wave patterns generated by the output acoustic power from the applicator. The results are shown in FIG. 8, where different angular directions were excited simultaneously to observe different patterns. Insonating a single direction at 6 W viewed longitudinally demonstrates a distinct collimated pattern of the ultrasound field of the sector was observed as shown in FIG. 8 (*b*). Similarly, the pattern by sonicating two lateral sector and all three directions are shown in FIGS. 8(*c*) and (*d*), respectively. Views with three and two active zones are shown in FIGS. 8 (*e*) and (*f*), respectively.

Experiments were conducted in ex vivo chicken breast and compared with simulation results. The input parameters for the FEM model were based on the experimental treatment parameters and tissue properties. A dual sectored device with transducer length of 10 mm was used for the experiment and simulations. The first and the second sector had the center frequency of 6.64 MHz and 6.7 MHz respectively. The tissue was sonicated for 1-2 minutes with water flow rate of 40-50 mL/min in the cooling balloon.

Figure 6:
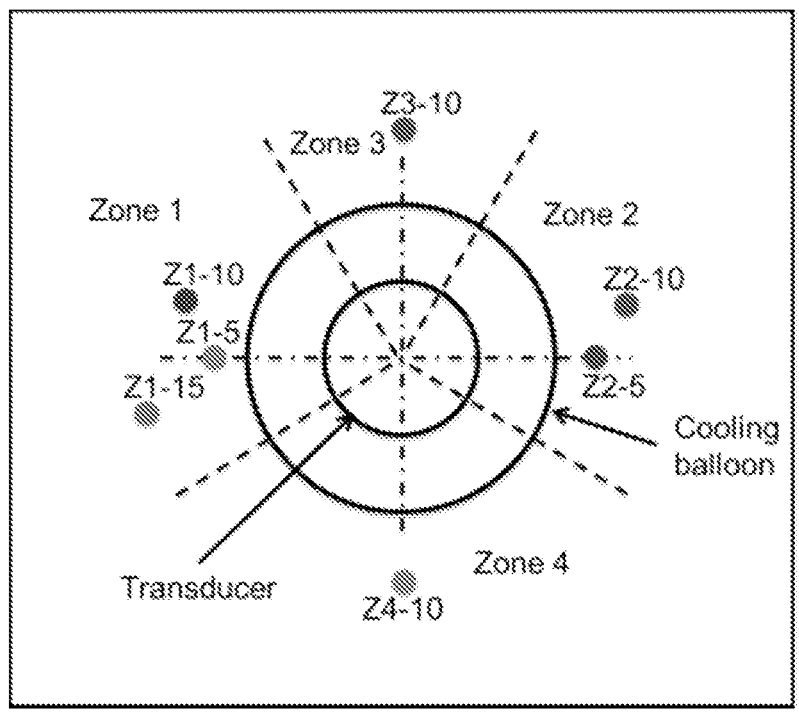
FIG. 6 is a top view of the location of the applicator and the various thermocouples in cross section.
Figure 7:
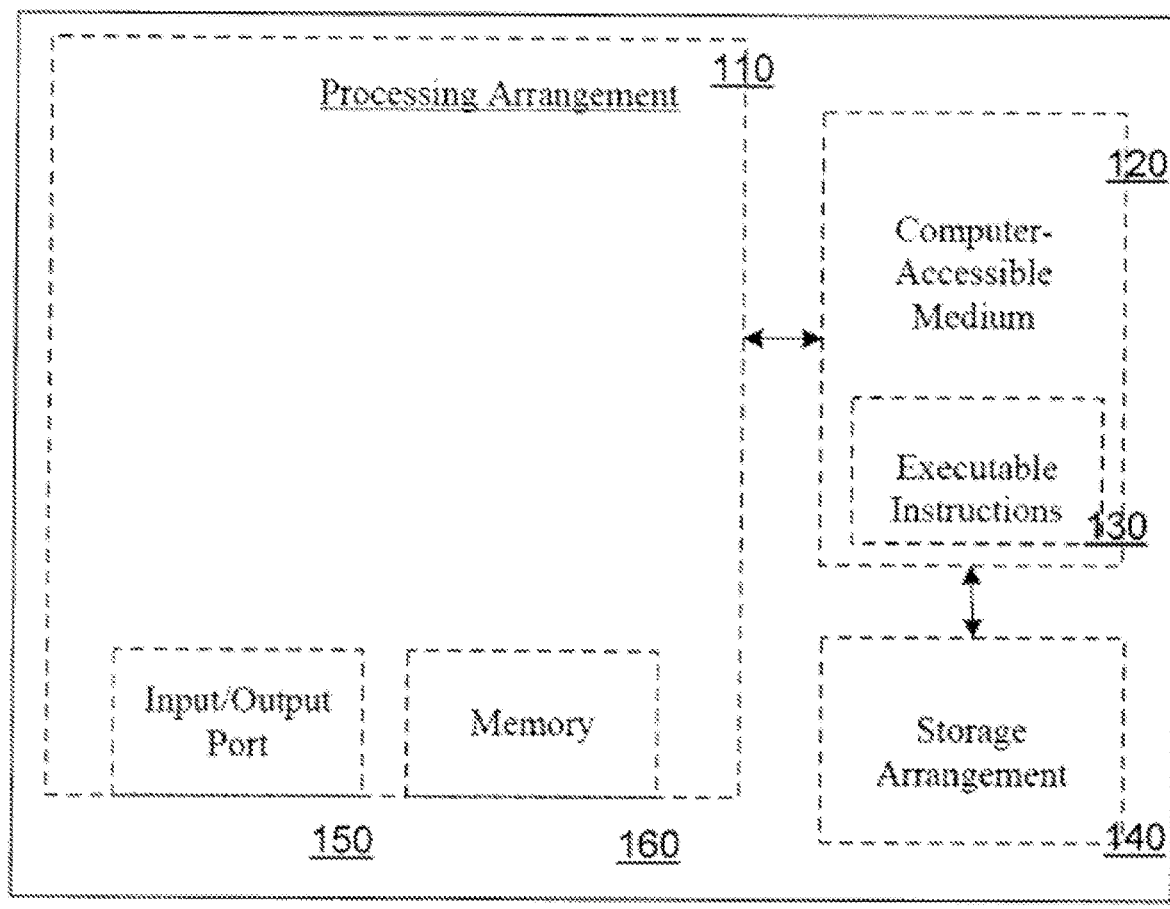
FIG. 7 illustrates a computer system for use with certain implementations.
Figures 9A, 9B, 9C:
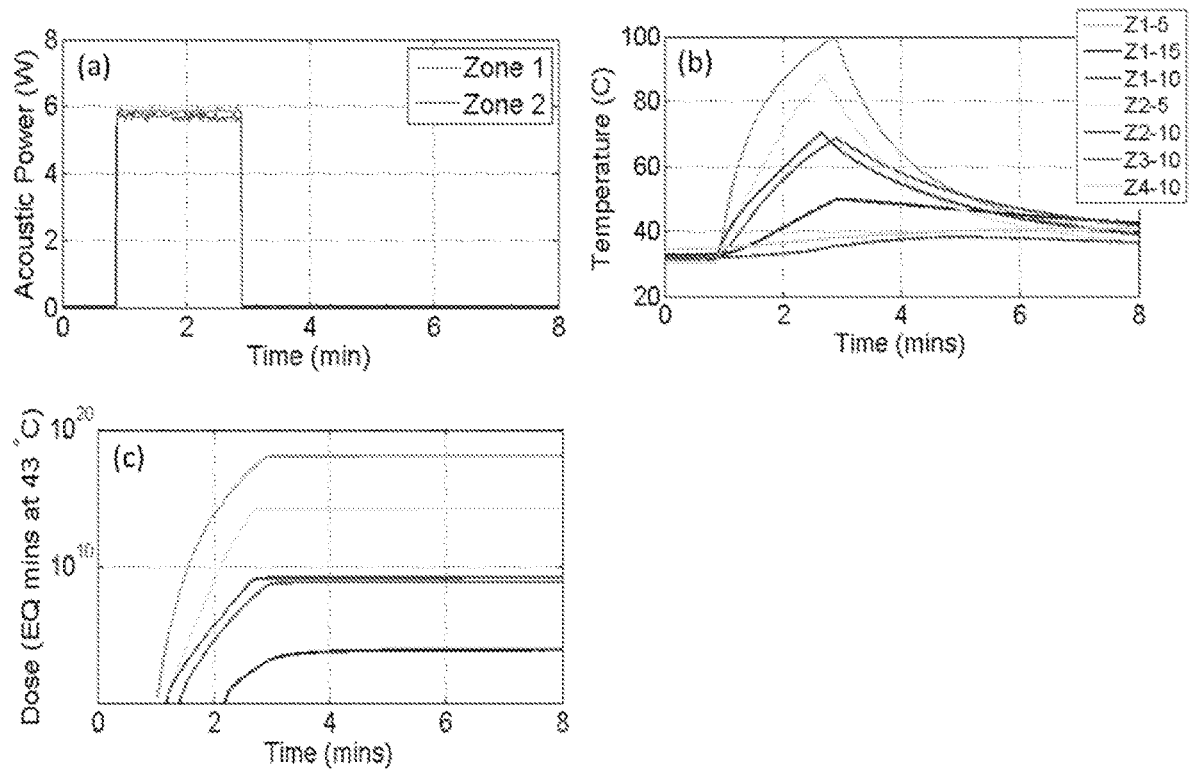
FIG. 9A Acoustic power output from the catheter based applicator for each of two angular directions during the treatment, (9B) temperature profiles recorded by the thermocouple sensors during the treatment, (9C) cumulative dose calculated from each of the thermocouple readings, (9D) gross pathology of the ablated zone with scale showing the lateral linear extent of the treatment zone.
Figure 9D:
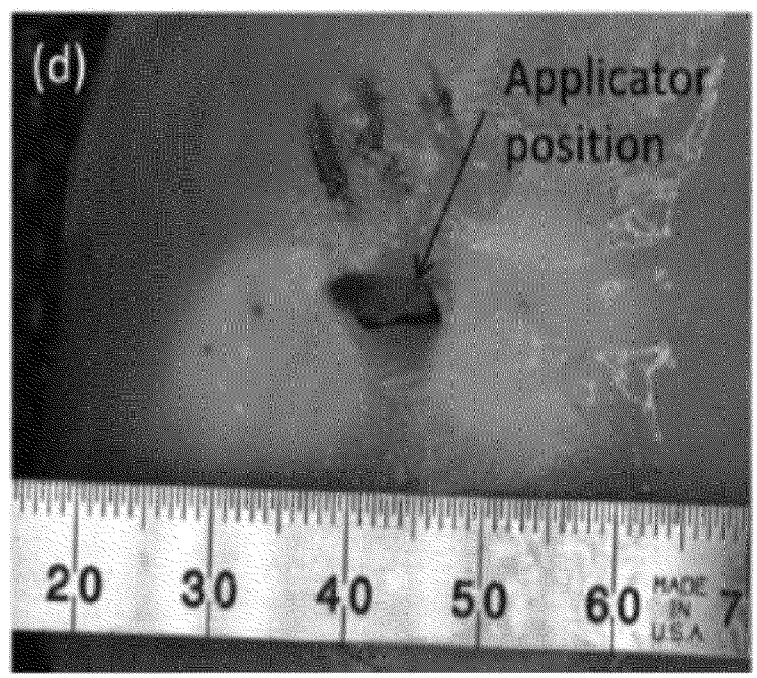

Acoustic power of 6 W was delivered to the tissue by each of the ultrasound ablation transducers in zone 1 and 2. The tissue was exposed to high intensity ultrasound for approximately 1-2 minutes as shown in FIG. 6A. The temperature recorded by the different thermocouple sensors is shown in FIG. 6(*b*), where the location of each thermocouple sensor with respect to the applicator was shown in FIG. 6. The dose calculated from each of the temperature sensor over time readings is shown in FIG. 9 (*c*). The legend for each of the temperature and dose curves shown in FIG. 6 corresponds to the thermocouple labels (Z1-5, Z1-15, Z1-10, Z2-5, Z2-10, Z3-10, Z4-10) shown in FIG. 6. The temperature increased monotonically with increase in exposure time and decreased after the power was turned off. Total dose delivered is in FIG. 6(*c*). Ablation pattern is shown in FIG. 6(*d*).

After exposing the tissue either in one or multiple directional locations, it was examined for gross pathology and visual inspection. An example of the gross pathology images are shown in FIG. 6(*d*). From visual inspection and differentiating treated region with respect to discoloration, the treatment region was laterally (perpendicular to the applicator) 15-20 mm long. Thermocouples located at 15 mm radially from the applicator showed a peak temperature of 52° C. and thermal dose of 6.4×10$^3$ EQ mins at 43° C. Necrosis occurs at 240 EQ mins at 43° C. and hence a minimum radius of 15 mm lesion can be obtained successfully with a 1 min treatment. The uniform discoloration of the treated zone indicates uniform ablation was obtained within the planned target zones as shown in FIG. 6 (*d*).

Figure 11A:
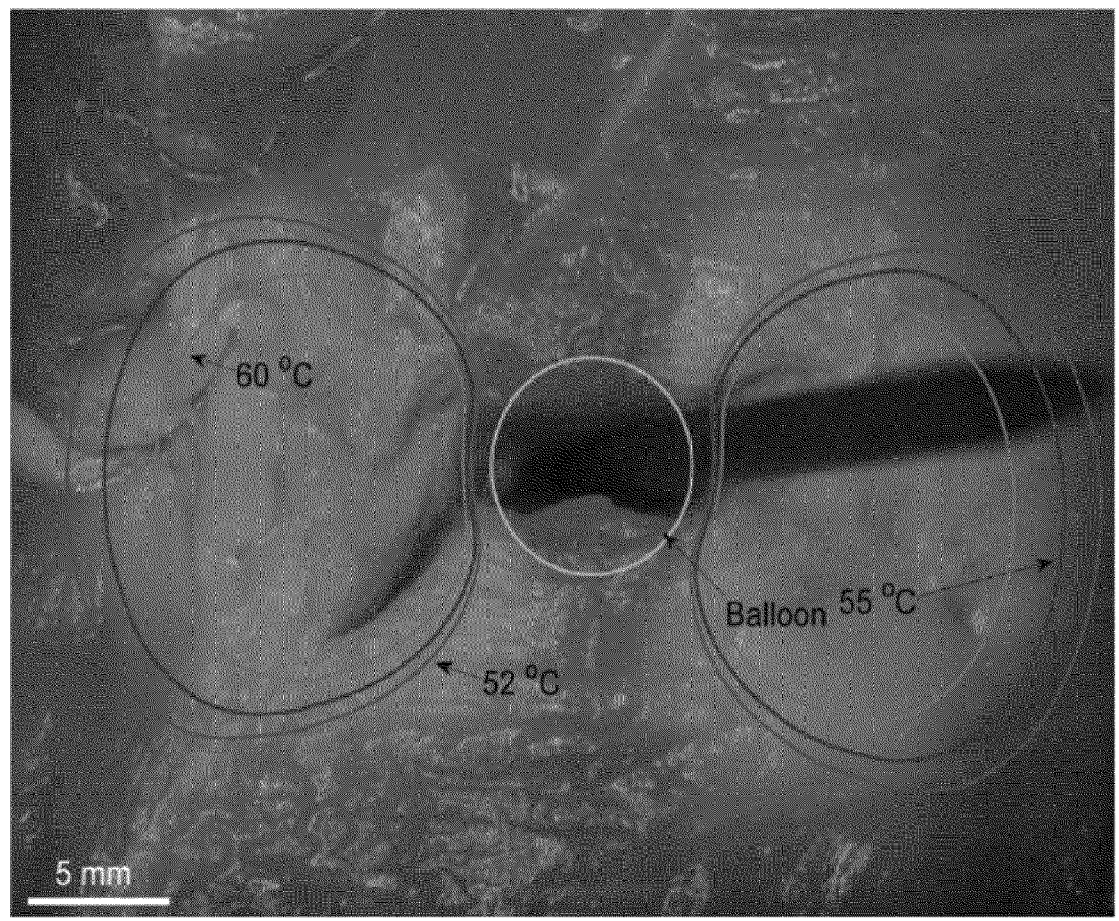
FIGS. 11A-11B Photographs of ablated tissue along an axial plane through the central axial direction through the applicator. (11A) Temperature contour and tissue ablation overlay. (11B) Thermal dose contour and tissue ablation overlay. Good correspondence can be observed between coagulated (identified by gross discoloration) tissue and temperature/thermal dose levels predicted by the model. Radial depth of tissue coagulation predicted by model (~14 mm) matches well with observations and experimental measurements.
Figure 11B:
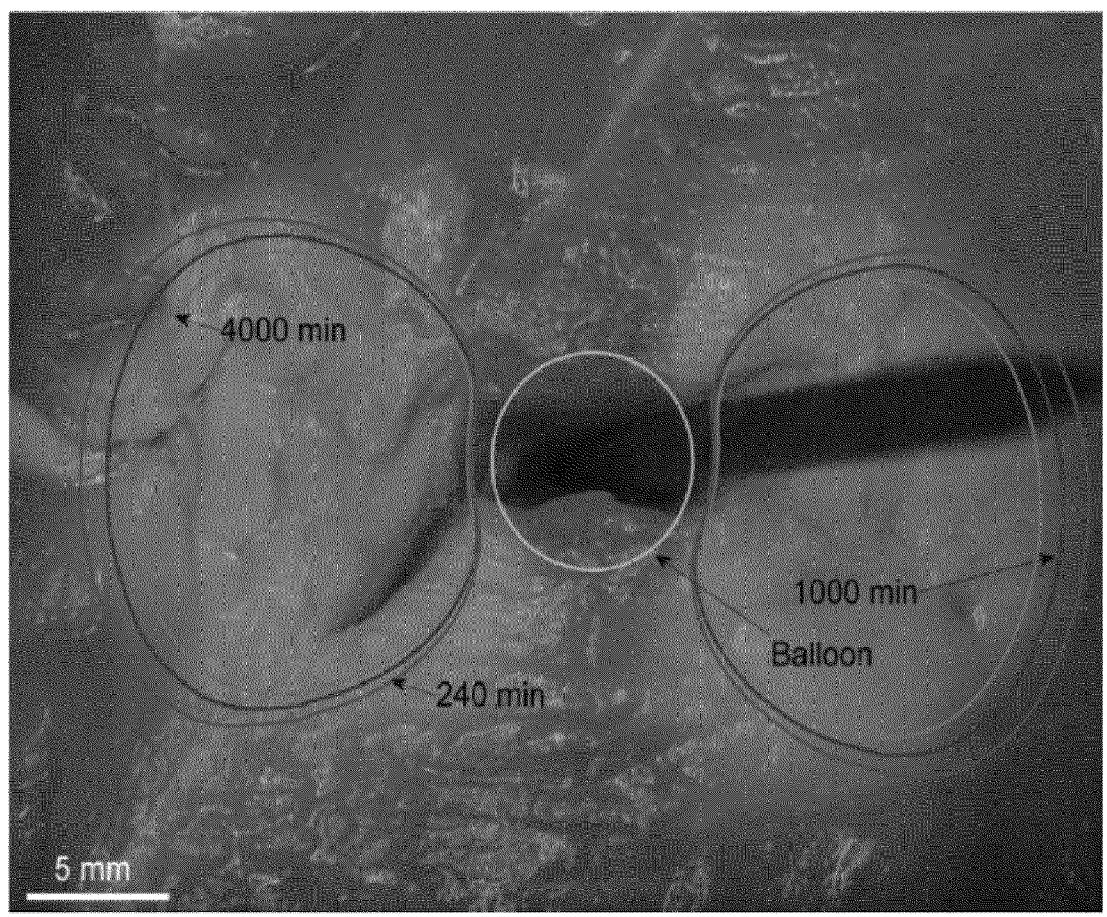
Figures 12A, 12B, 12C, 12D:
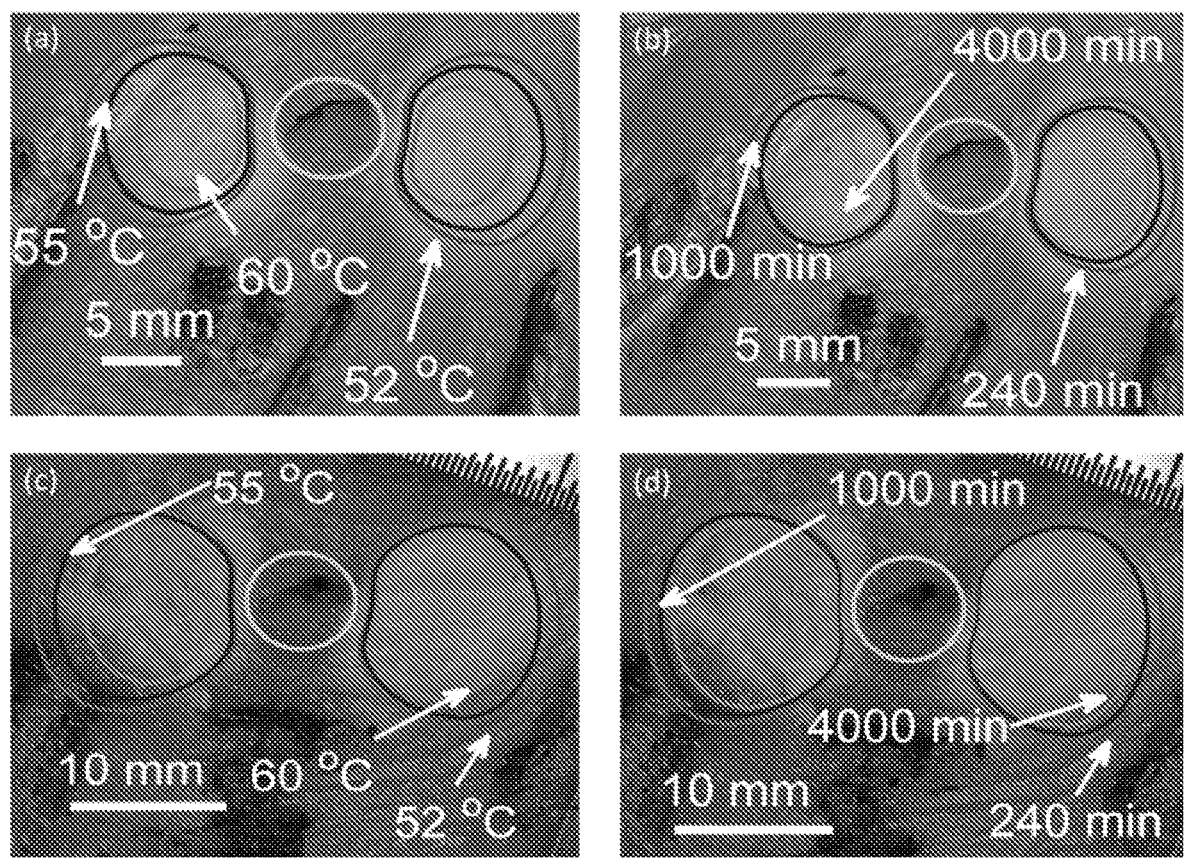
FIGS. 12A-12D Comparison between gross tissue pathology observed during ablation of ex vivo chicken breast muscle and temperature (left), and dose (right) predicted by modeling. Cases: (12A, 12B) Acoustic power=4, 4 W and time=2 min. (12C, 12D) Acoustic power=5, 5 W and exposure time=2 min.

Additional experiments were performed to form different ablation patterns as per planned treatment and directly compare with simulation results. The comparison between the experiments and the simulation result for delivered acoustic power of 6 W from both the sectors in zone 1 and 2 is shown in FIGS. 11A-B. The images of the ablated tissue are in the axial plane through the central axial plane direction of the applicator. The comparison between experimental and simulation results with respect to temperature and dose profiles spatially for treatment duration are shown in FIGS. 11 (*a*) and (*b*), respectively. The comparison between the experimental and simulation results for the acoustic power of 4 W and 5 W (equal power applied to both zone 1 and 2) are shown in FIGS. 12(*a*)-(*d*). The exposure time was 2 minutes for both the cases. It can be observed that more power produced a larger ablated region. Good correlation was observed between gross tissue pathology and both the temperature and dose contours. The region of tight coagulation seen on photographs of ablated tissue corresponds well with 60° C. contour predicted by the models.

Figure 13A:
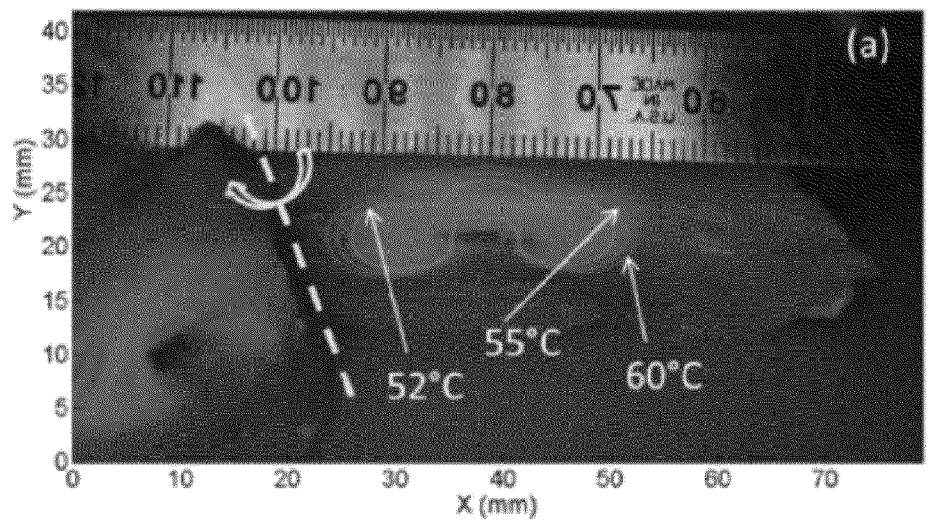
FIGS. 13A-13B Comparison between gross pathological tissue damage observed during ablation of ex vivo chicken breast, and temperature (13A) and dose (13B) predicted by modeling. Acoustic power=7, 7, 3 W and exposure time=2 min.
Figure 13B:
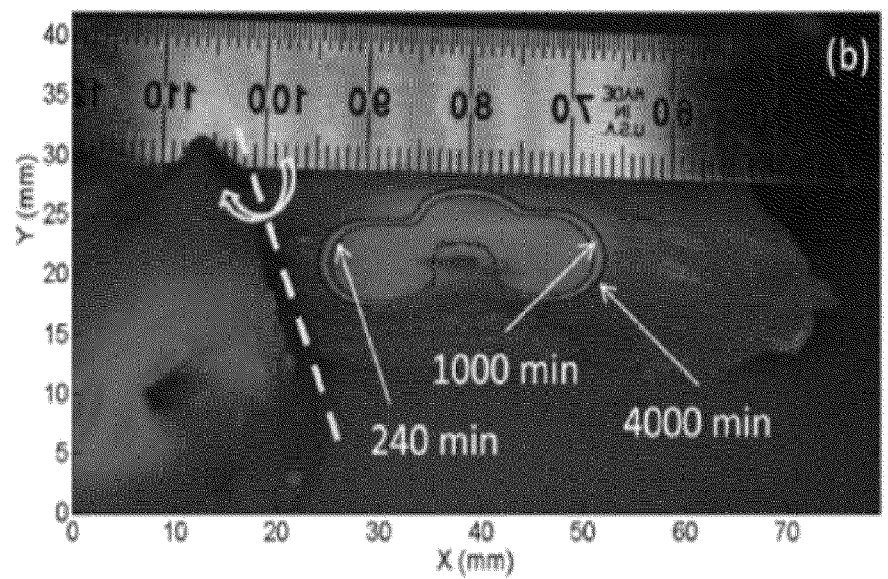
Figure 14A:
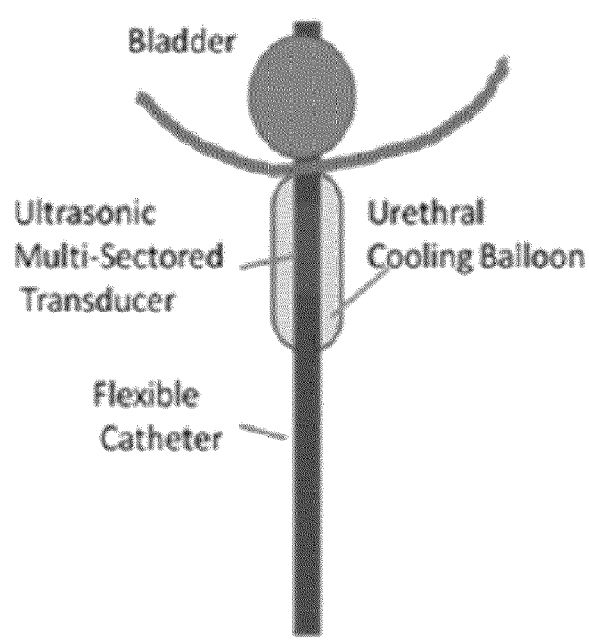
FIG. 14(a) Schematic of the Insertion of the treatment applicator with the anchor balloon held against the bladder neck, 14(b) schematic of the urethra showing the endopelvic fascia and connective tissue and 14c schematic of normal anatomy of urethra and its supporting structures obtained from MR Images. [SP=symphysis pubis, V=endovaginal coil, R=rectum, ATFP=arcus tendlneus fasciae pelvis, pu=pubourethral ligament, pe=periurethral ligament, pr=puborectal sling).
Figure 14B:
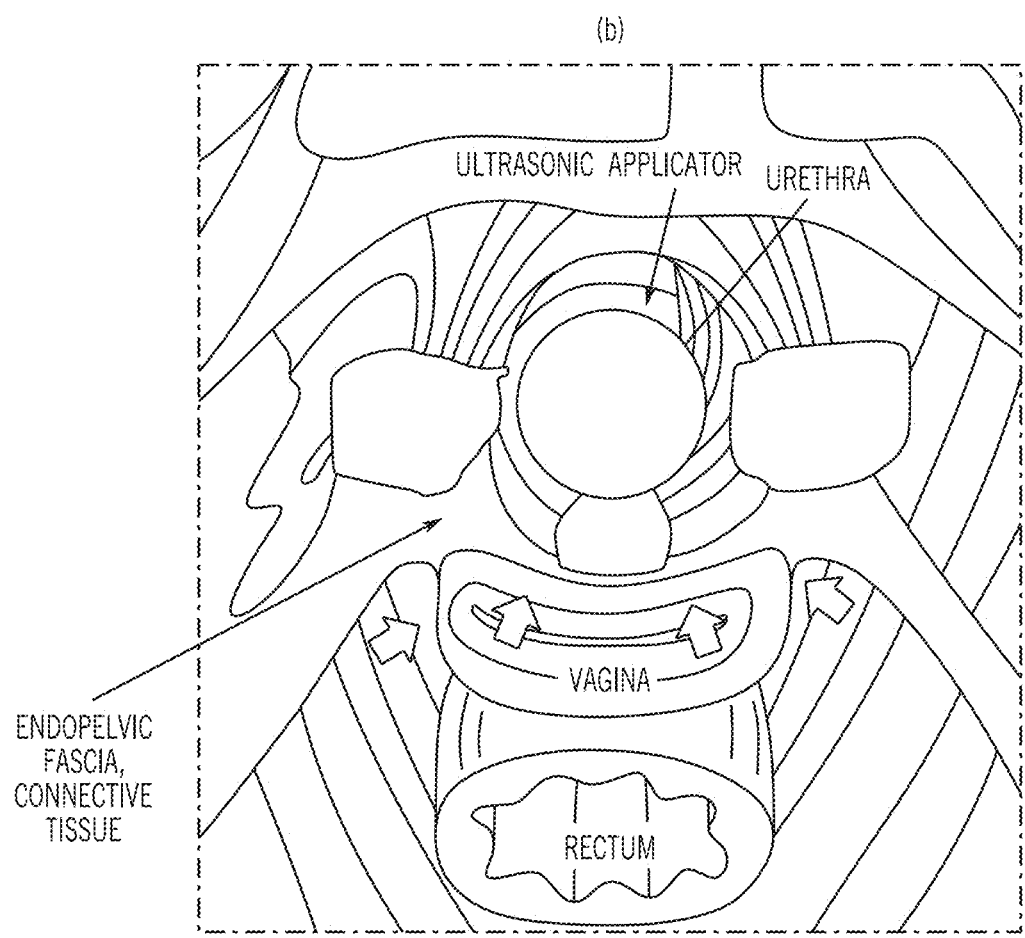
Figure 14C:
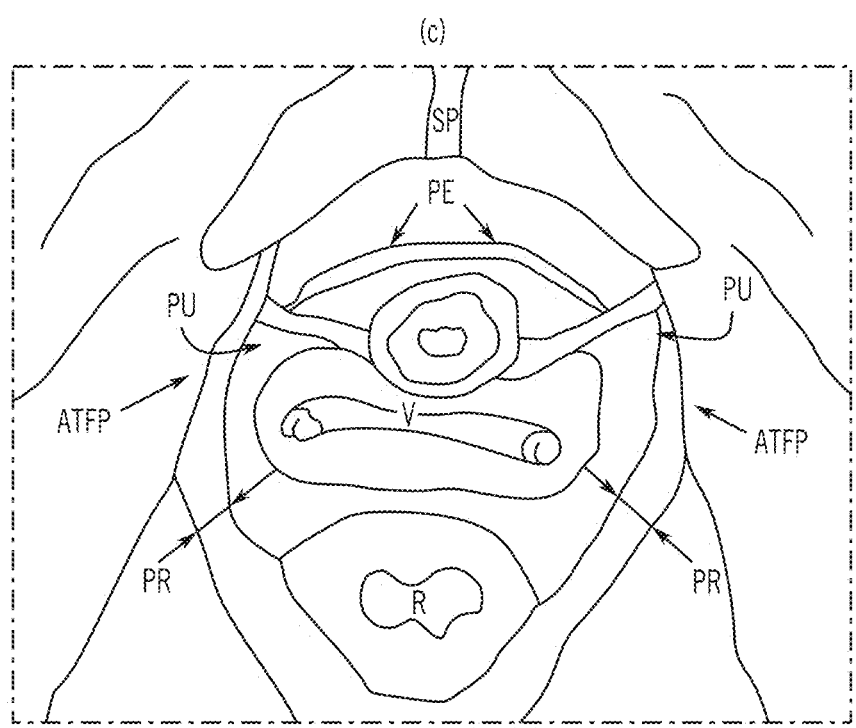

Experiments were also performed for simultaneous activation of three angular directions. Acoustic powers of 7 W, 7 W and 3 W were delivered to the tissue by the sectors in zones 1, 2 and 3, respectively. The central zone was excited with lower power purposefully to obtain the different treatment pattern. The experimental and simulation results for temperature and dose are shown in FIGS. 13(*a*) and (*b*), respectively. The yellow dotted lines indicate the plane of tissue cut and the curved arrow shows that the left part of the tissue was flipped open to visualize the ablated region clearly. The simulation results are displayed as contours and clearly demonstrate good agreement with the experimental results. It can be observed that zones 1 and 2 have more radial depth of penetration than in zone 3. This is due to the designed differential power delivered to the tissue of those treatment zones.

All the experimental results show very good agreement with the simulation results. The results clearly demonstrate that the tissue in zone 4 was not at all treated or damaged. In all the experiments, the tissue in the deactivated zones clearly showed no thermally induced damage. Therefore, the current technology can be used efficiently to ablate planned regions while sparing nearby veins/vessels. Such minimal invasive thermal therapy procedure may not be feasible with other currently available technologies.

Experiments were performed to investigate the feasibility of using directionally sectored tubular ultrasound transducer to create multi-angular ablation patterns in tissue. The proposed technology has achieved accurate directional acoustic energy to the planned locations without damaging the surrounding tissue. The experimental results were compared with simulation results for verification. The simulation was performed using commercially available finite element method software to solve the bio-heat equation with appropriate boundary conditions. The experimental results demonstrated that the directionality and shape of the ablation zone can be controlled using catheter based high intensity multi-directional ultrasound transducers. The transducers enabled creation of desired ablation patterns without damaging the nearby tissue and verified through both gross pathology inspection and measured data.

Ex vivo chicken breast tissue samples was used here to eliminate the effects of blood flow for this feasibility and preliminary study. We plan to conduct future experimental studies using the proposed technique for treating in vivo tissues and study the effects of blood flow on the results obtained as compared with the results in this study. For the in vivo study we plan to include the blood perfusion terms into the bio-heat equation model and solve using finite element methods. More exposure time or higher acoustic power may be needed for in vivo tissue compared to time needed in this study to achieve similar treatment volume in both cases since the blood flow will act as a coolant during the in vivo treatment. Parametric characterizations of this dependency will be studied and developed for future treatment use.

2. Treatment Applications

One embodiments relates to methods for treatment. Certain embodiments of the device described above are able to create treatment zones of different shapes according to the anatomy of the patient by controlling the power deposition in each angular sector of the multi-sectored transducer. Therefore, physiological issues such as disease or conditions, for example SUI as further discussed below, can be treated using the concept of personalized medicine. The anatomy of every human differs from person to person and the various embodiments will be considering such variations to deliver optimized treatment according to the anatomy. For some applications, the complete treatment time is 2 minutes in a single placement of applicator—something not available with the current thermal therapy procedures. Every delivery occurs in only one step (not multiple locations/insertions), reducing the operator variability during procedure. Such controllable thermal ablation technique does not presently exist for many thermal treatments, such as thermal treatment of SUI. Unlike other thermal therapies such as RFA the proposed technology does not require to pass electric current passed into the patient's tissue, isolating the patient electrically. Moreover, various embodiments are a noninvasive procedure, with no needles or incisions.

3. Stress Urinary Incontinence Treatment

The feasibility of using a catheter based ultrasound transducer system was shown above with regard to ex vivo use in chicken. However, one in vivo application of importance is the treatment of Stress Urinary Incontinence (SUI). Stress Urinary Incontinence (SUI) is unintentional loss of urine prompted due to physical movement or activity such as coughing, sneezing or heavy lifting which exerts pressure on the bladder.

One technique described herein uses high intensity directional ultrasound ablation to achieve superior results remodeling the endopelvic fascia. The primary advantage of high intensity ultrasound is that it is more penetrating and controllable than RF, and may affect thermal remodeling of the collagenous structure of the endopelvic fascia (noninvasively) by propagating acoustic energy through the urethra and deep into the endopelvic fascia. The proposed procedure eliminates the use of any incision for the thermal ablation and can produce the hammock effect of a sling.

The approach requires urethral insertion of a catheter-based ultrasound applicator with a multi-sectored tubular radiator, such as described above. Acoustic energy is targeted specifically to the endopelvic fascia and connective tissue at the lateral aspects of the urethra without the need for an incision. The resultant thermal remodeling of the collagenous structures in the endopelvic fascia will restore the structure to a more normal anatomy, without damaging the tissue structures of the urethra or vagina. It is believed a multi-sectored transurethral ultrasound applicator can generate penetrating and selective thermal therapy while urethral mucosa is protected with cooling. This provides a minimally-invasive framework for targeting the endopelvic fascia, more accurately and effectively than current RE approaches, and less-invasive than surgical techniques.

As described in further detail, one embodiments relates to a cost-effective, non-invasive and feasible approach for thermal treatment of SUI using transurethral high intensity ultrasound. All current surgical interventions involve incisions or needle insertions through the urethral wall or vaginal wall, in some instances depositing or placing implants.

In one embodiment, modification of the endopelvic fascia may be achieved in a simple, non-invasive manner with high intensity concentrated ultrasound via a transurethral approach. There currently exists clinical evidence that heating the pelvic floor and/or tissue surrounding the bladder neck to produce shrinkage to stabilize the urethral structure has a significant and positive clinical effect. Initial laboratory testing for this application has been performed which indicates that the catheter based ultrasound technology described above can create lesions of the appropriate dimension to affect that change.

This approach will (1) selectively heat the anatomic structure (endoplevic fascia) to be treated (mid-urethra); (2) map the treatment focal depth and focal zone; (3) apply acoustic energy to raise the temperature of selected tissue regions within the endopelvic fascia to 55° C. to 75° C. for a short time period to affect immediate tightening and remodeling (stimulating fibroblasts) of the collagenous structure of the endopelvic fascia. The approach has the capability of accurately deliver acoustic energy to endopelvic fascia with controllable directivity and directionality.

i. Computer Modeling

Figure 15A:
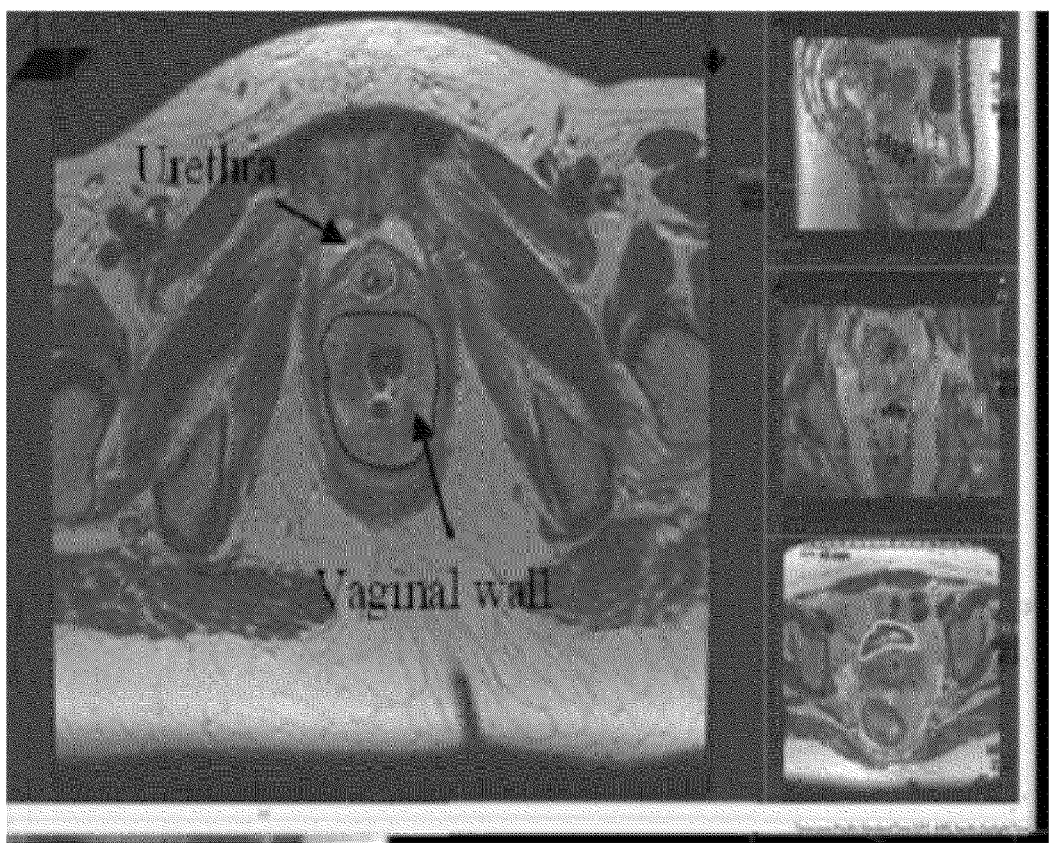
FIGS. 15A-C Oncentra contouring software platform. 15(A) Axial plane, 15(B) sagittal plane, 15(C) 30 reconstruction of contoured organs.
Figure 15B:
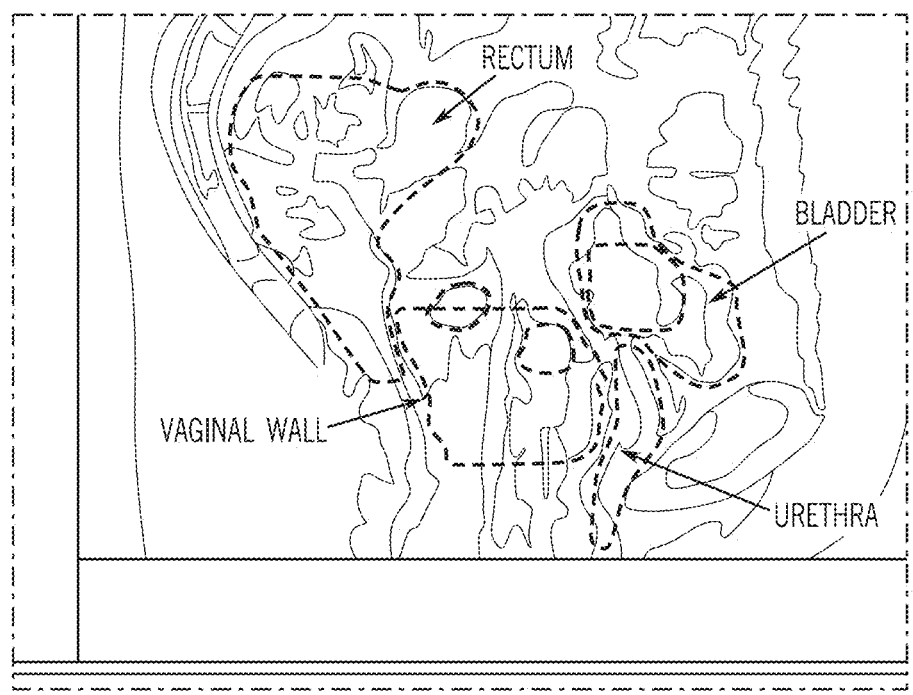
Figure 15C:
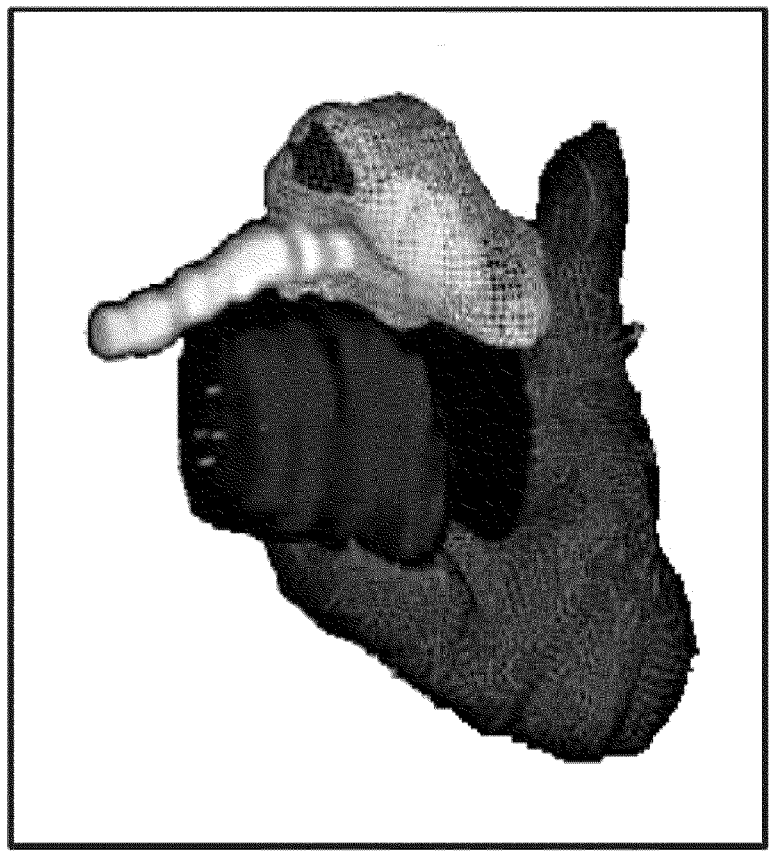

In one embodiment, a treatment for SUI is provided. One method of treatment for SUI uses direction ultrasound ablation. Computer simulations were run that simulated using the three-dimensional (30) finite element model (FEM). The anatomical geometry from representative patients was used to build the 30 models and used for constructing the FEM mesh. The simulation methods were as follows:

Anatomical model geometry: Serial axial MRI scans from representative patient cases were segmented using a contouring software program to delineate anatomical structures such as vaginal wall, urethral mucosa, bladder, etc. as shown in FIG. 15A-C.

Applicator: The applicator was assumed to have a single tubular transducer (diameter=3.5 mm), with three active sectors. The side sectors were assumed to have an angle of 90°, while the central sector aimed towards the vaginal wall was assumed 62°. The cooling balloon was assumed to have a diameter of 7 mm. The applicator was placed along the urethral axis with the applicator tip was placed 10-12 mm proximal to the bladder neck.

Biothermal model: Pennes equation was assumed to model heat transfer. Blood perfusion was assumed to be homogeneous in tissue and was reduced to zero where the local temperature was raised above 55° C. Cooling water temperature was assumed to be 20° C., and the cooling coefficient was set to 4500 W/m$^2$/K. Models were solved using Corn sol 3.5a (Cornsol Inc.)

Acoustic model: A geometric approximation was used to model acoustic intensity which was assumed to be inversely proportional to the radial distance from the applicator (decay from the surface intensity with a factor of 1/r). The transducer frequency was set to 7 MHz. Nominal value of acoustic attenuation was set to 46 Np/m, and was doubled for vaginal wall. Temperature dependent changes in attenuation were ignored.

Figure 16:
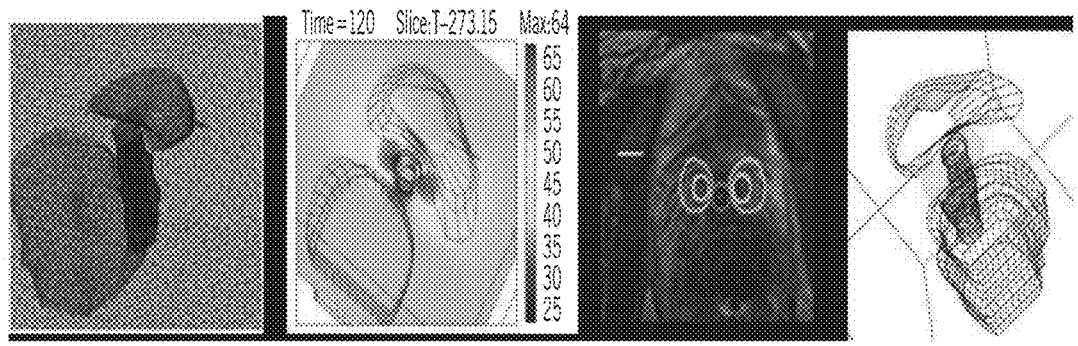
FIG. 16 Schematic diagram to depict work flow during 30 patient specific finite element modeling processes, Left to right: Segmentation>FBM Mesh>Power Deposition>Thermal 3D Profile FIG. 17 SAR patterns from two (left) and three (right) sectored transducers.

The numerical model was meshed by using finite elements to discretize the solution space and appropriate boundary conditions were imposed. Three-dimensional temperature profile was estimated using the FEM. Using the FEM results, contour plot of the temperature profile followed by the thermal cloud was constructed for visualizations. The flow for these processes is shown in FIG. 16. A nonlinear, implicit solver with variable time steps was used to solve the ablation problem.

ii. Results: Patient Specific Simulations (1) Patient 1

Figure 17:
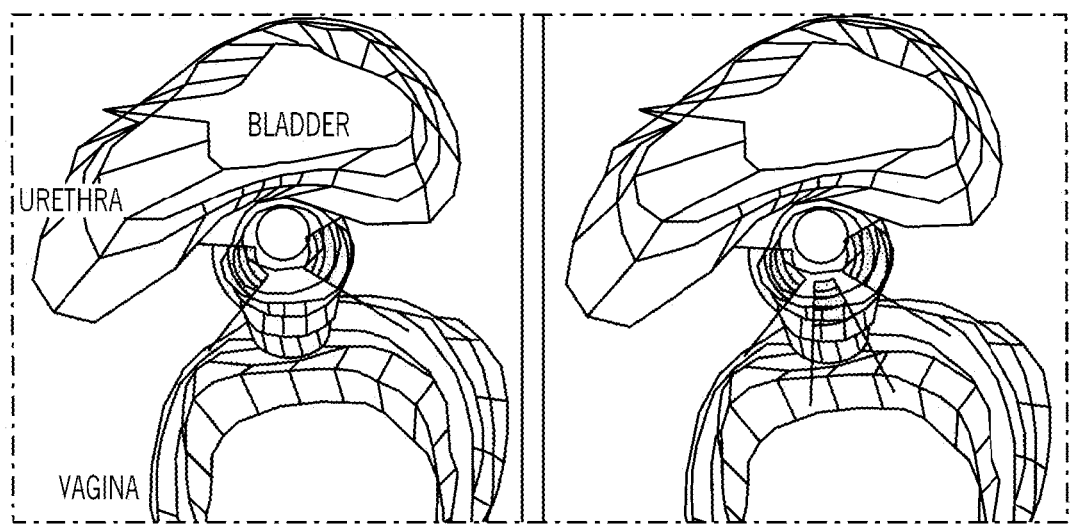
Figure 18:
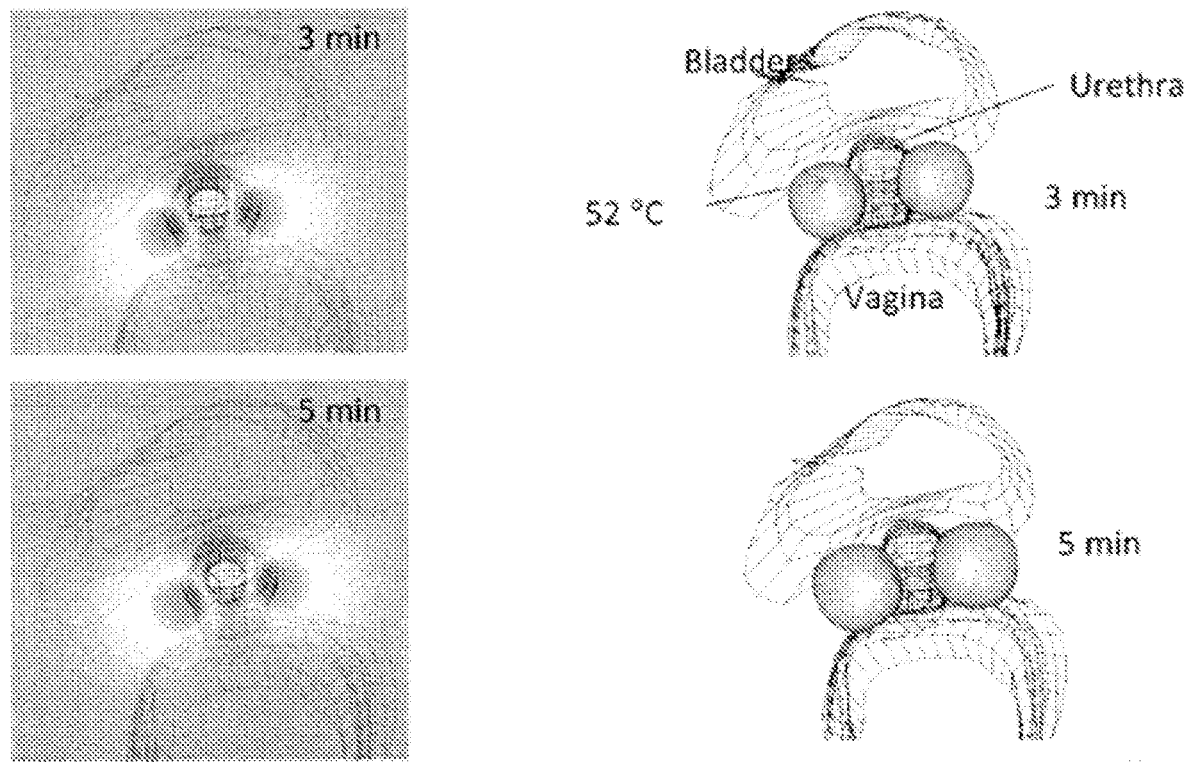
FIG. 18 Ablation with two sectored (90°) device sonicating with acoustic power=4.7 W FIG. 19 Ablation with triple sectored applicator (center sector=60°). Acoustic powers=4.7, 4.7, 1.2 W FIGS. 20A-D 3D temperature distributions obtained for a representative patient anatomy. The bladder is shown in black, vaginal wall in medium grey, urethra in black wireframe, and the applicator in dark grey. 20(a) Evolution of 45° C. (gray: safety), 52° C. (light grey: necrosis) and 60° C. (dark: coagulation) over a 2 min sonication time for acoustic powers of 6-6-0 W, with perfusion of 2 kg/m$^3$/s. 20(b) Comparison of 52° C. contours obtained after 2-min sonication at 6-6-0 acoustic watts for perfusion values of 0.5 kg/m$^3$/s (light) and 5 kg/m$^3$/s (dark). 20(c) Comparison of 52° C. contours obtained after 2-min sonication at 6-6-0 acoustic watts (light) and 4-4-0 acoustic watts (dark), perfusion=2 kg/m$^3$/s. 20(d Comparison of 52° C. contours obtained after 2-min sonication at 6-6-0 acoustic watts at perfusion of 2 kg/m is when using applicator with 14 mm (light) and 10 mm (dark) long transducers. Note the longer penetration depth, but shorter axial length for the latter.
Figure 19:
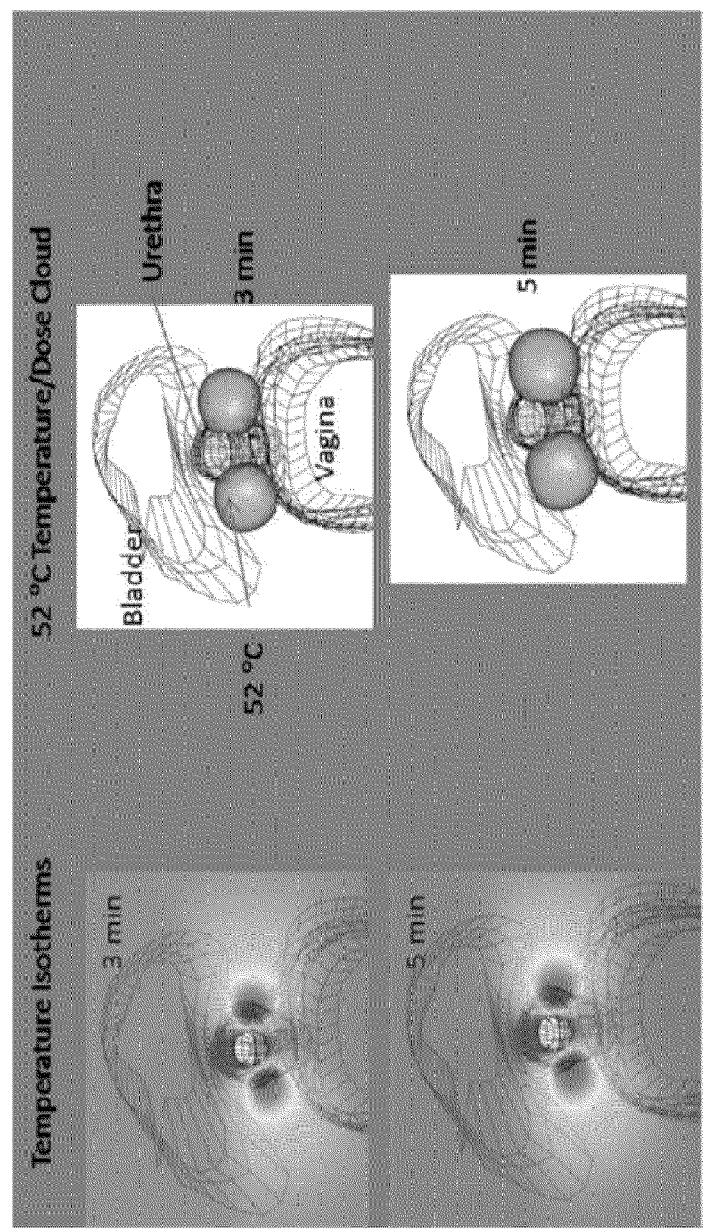
Figure 20A:
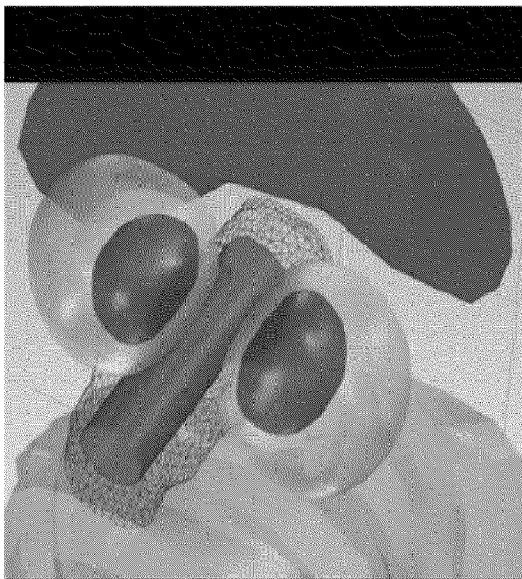
Figure 20B:
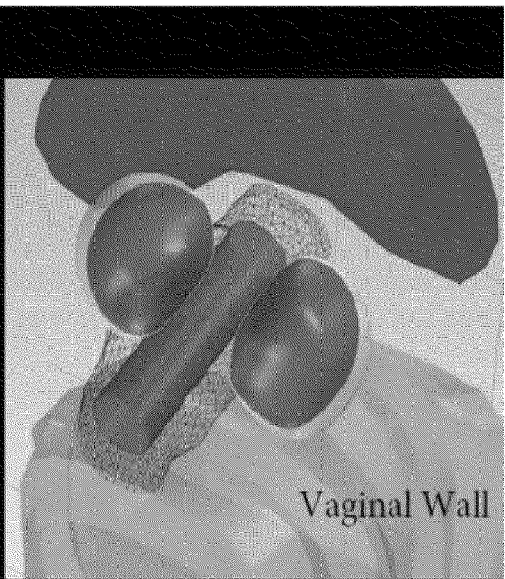
Figure 20C:
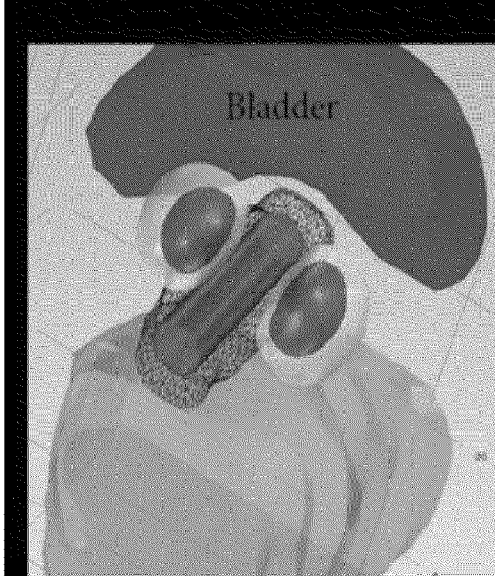
Figure 20D:
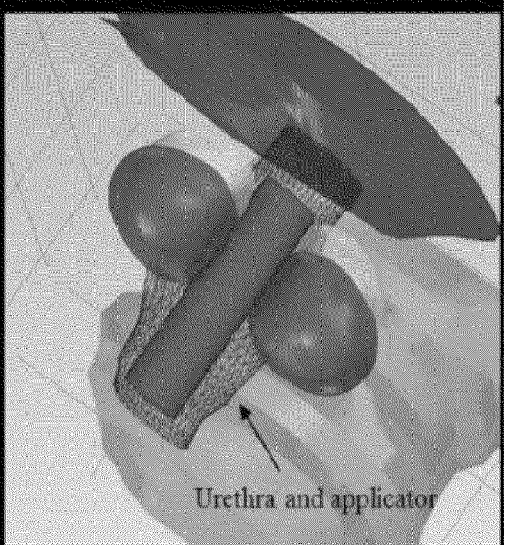

Using FEM, specific absorption rate (SAR) was estimated for two and three sectored transducers as shown in FIG. 17. It is believed that the three sectored transducer may be helpful to treat different tissue thickness at different directions in a single ablation. The simulated treatment patterns (temperature isotherms) using two and three sectored transducers are shown in FIGS. 18 and 19, respectively. The two sectored transducer had each sector of 90° and the three sectored transducer had two 90° sectors and the middle sector was 60°. The treatment patterns were shown at time step 3 mins and 5 mins for both transducer types. For both the simulation acoustic power of 4.7 W were used for the larger sectors and 1.2 W was used for the middle sector on the three sectored transducer. The temperature clouds for each of the cases are shown in FIGS. 18 and 19.

The three-dimensional temperature distribution for a representative patient anatomy is shown in FIGS. 20A-D using a two sectored applicator. The simulated results showed the different regions such as necrotic and coagulated tissue for the different treatment cases. The necrotic, coagulated and safety tissue regions were identified using the temperature profile given by the FEM results. The simulation results were also shown for transducer of length 10 mm and 14 mm. The different length of the transducer may be helpful for treating patients with shorter or longer urethra.

(2) Patient 2

Figure 21:
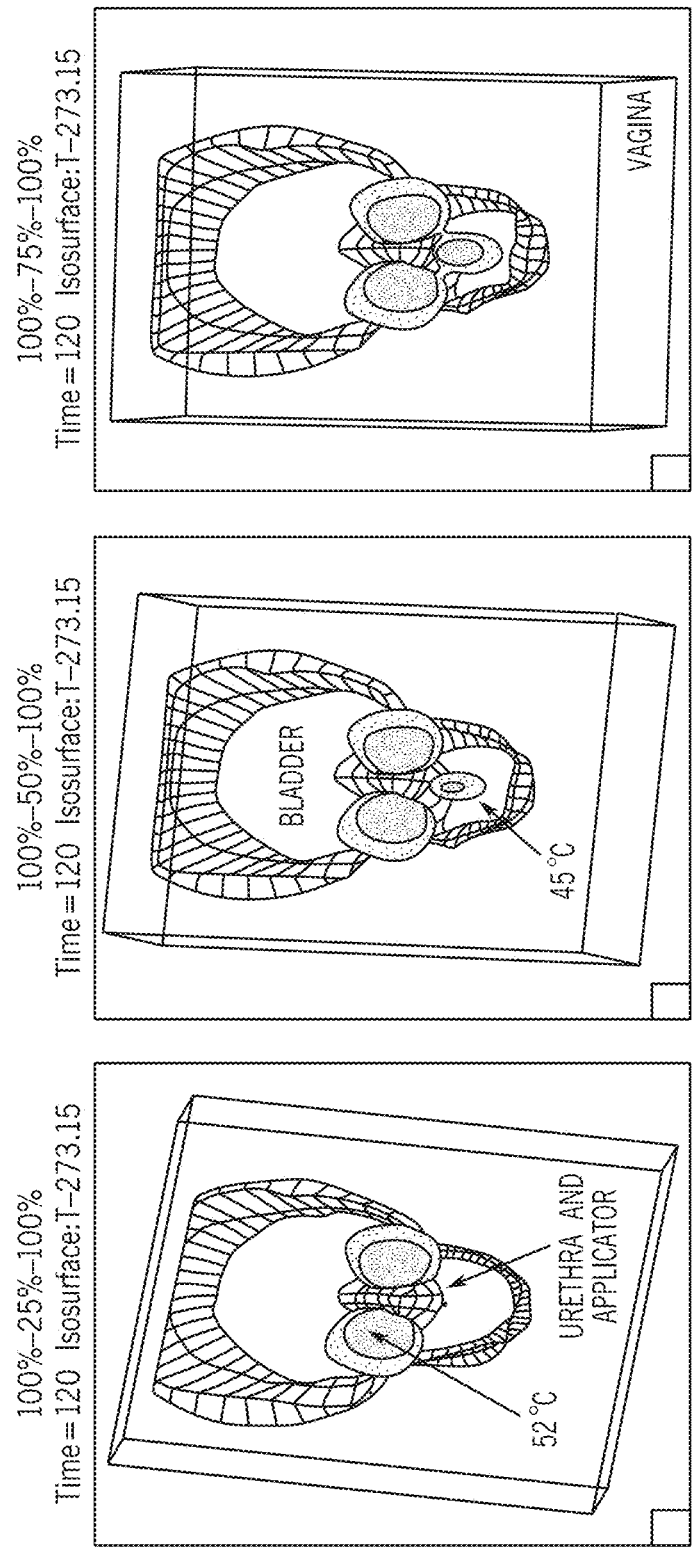
FIG. 21 Ablation volumes obtained during 2 min sonications with maximum acoustic power of 7.05 W (10 mm transducer segment). Power weighting between sectors was set to 100%-25%-100% (left), 100%-50%-100% (center) and 100%-75%-100% (right). Power values to the central sector can be varied to vary penetration depth.
Figure 22:
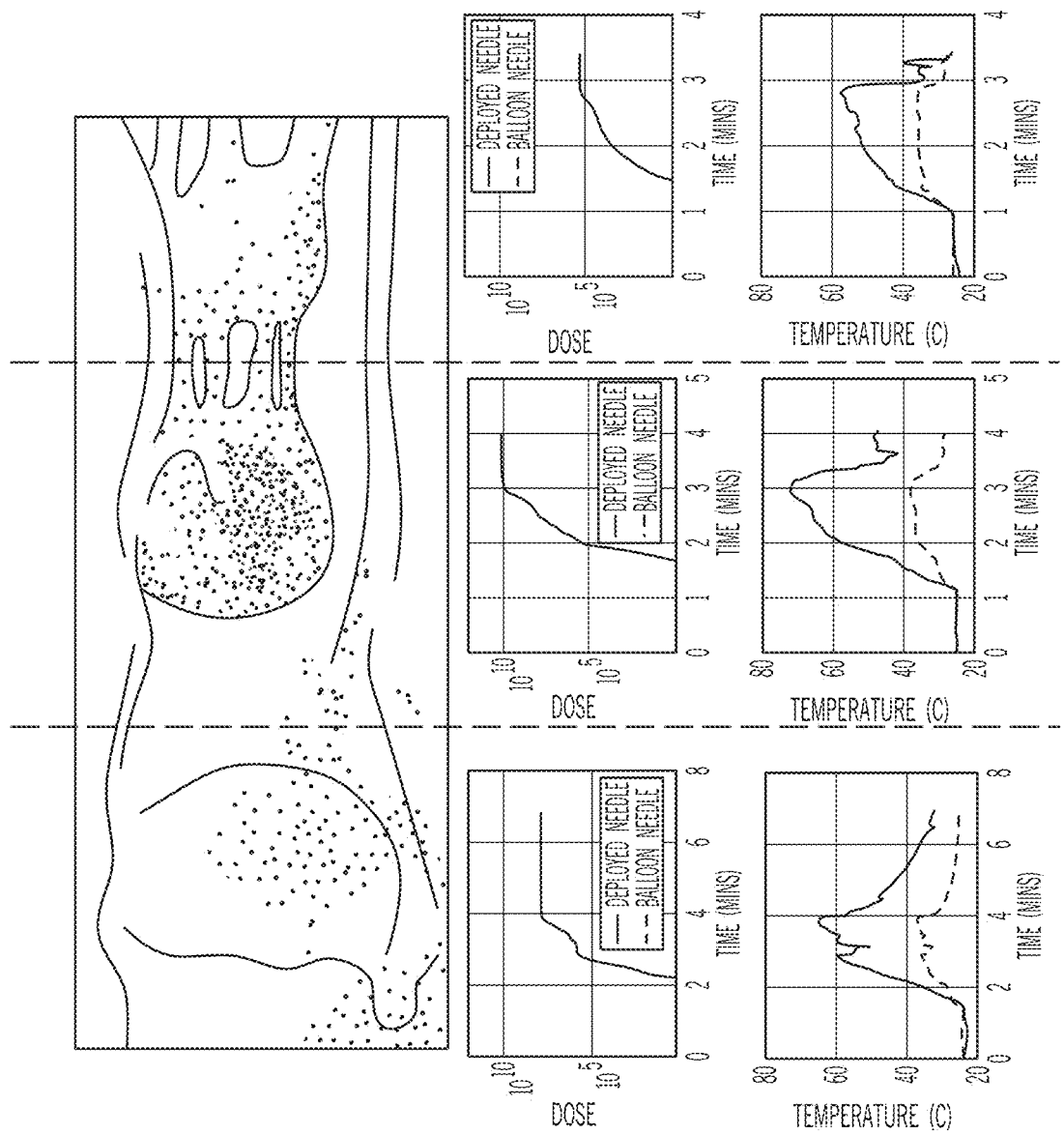
FIG. 22 Tissue gross pathology and thermometry for the excised pig GU tract on the tissue holder after treatment. The graph Is each column refers to data from each treatment. The first, second and third rows refer to image of treated region, dose recorded by the deployed and balloon thermocouples, and temperature profile of the deployed and balloon thermopiles, respectively.

The second patient's anatomy is shown in FIG. 1523. Hence, power levels to the center sector were varied (FIG. 22.). The simulated treatment result is shown in FIG. 21. It was observed that by varying the power in the central sector of a three sectored transducer changed the penetration depths for the treatment.

iii. Results: Comparing Models and Ex Vivo Experiments

Experiments were conducted in ex vivo chicken breast maintained between 33-35° C. and compared with simulation results. All the experimental parameters were used as input parameters for the FEM model. A dual sectored device with transducer length of 10 mm was used for the experiment and simulations. The first and the second sector had the center frequency of 6.64 MHz and 6.7 MHz respectively. The tissue was sonicated for 2 minutes with water flow rate of 45 mUmin in the cooling balloon. The chicken breast tissue was used for experimental verification and validation. The same tissues with all the appropriate acoustic and thermal properties characteristics for these tissues were also modeled using the computer acoustic and thermal models to predict the thermal heating distributions for the exact tissue properties and geometries that we studied experimentally. This provided clear evidence of corroboration between actual experimental results and representative theoretical models which have previously been verified in other tissues—e.g. prostate.

The comparison between the experiments and the simulation result for delivered acoustic power of 6 W from both the sectors is shown in FIGS. 11A-B. The images of the ablated tissue were along the axial plane through the central axial plane through the applicator. The comparison between the experimental and simulation results for the acoustic power of 4 W and 5 W are shown in FIGS. 12 (a)-(d). Good correlation was observed between tissue damage and temperature and dose contours. Region of tight coagulation seen on photographs of ablated tissue corresponds well with 60° C. contour predicted by the models.

iv. Results: Parametric Study

Patient case #1 was utilized as representative model geometry. A parametric study was carried out using the information for patient one. The Input Parameters were Perfusion=0.5-5.0 kg/m$^3$/s, Time=0-10 min, side sector acoustic power=2-8 W, central sector acoustic power=0-3 W, Transducer length=14 mm. Acoustic power settings of 6, 6, 3 W were found to produce clinically relevant thermal ablation and hence used as a representative case to show radial and longitudinal temperature/thermal dose profiles. Radial and longitudinal dimensions for safety margins (T=45° C., EM43° C.=10 min), necrosis (52° C., 240 min), and tight coagulation (60° C., 1000 min) have been included. For the parametric study, findings from the tables can be summarized as:

For acoustic power of 2, 2 0 W, 10 min exposures may be required to treat radial distances in excess of 10 mm.

With 6, 6, O and 4, 4, O W, it may be possible to treat 10-15 mm radially within 2-5 min. Safety margins may extend 5 mm beyond this range.

With 8, 8, 0 W, targets can be treated within 2 min, but high maximum temperatures exceeding 90° C. were estimated.

Heating due to side and center sectors are decoupled to a large extend and radial or longitudinal heating due to the side sectors is not significantly impacted by powering the center sector to 0-3 W.

With 2 W acoustic power to the center sector, 0-12 mm radial depths can be treated.

Excised pig GU tract tissue experiment

Excised pig GU tract were obtained from the University of Illinois slaughter house to conduct the preliminary experiment before conducting the in vivo experiment. The main aim of the tissue experiment was to verify the feasibility of inserting the treatment catheter through the urethra for treatment, and also get familiar with the GU tract anatomy. The length of the urethra in the excised pig GU tract used for the laboratory experiment was approximately 11 cm.

The tissue was treated at three different locations at mid-to-higher acoustic power levels to deliver greater thermal dose. This acoustic power range is typically from 6 to 10 acoustic watts, depending upon target volume and thermal dose target desired. The high acoustic power levels were used purposely so that the treatment may be identified visually. The second goal of the experiment was to determine if the deployed thermocouple would adequately penetrate through urethral wall to measure temperature of the treatment region. For the experiment the tissue was mounted on a custom GU tract holder. The semi-cylindrical GU tract tissue holder helped to mimic in vivo intact position. After the treatment the tissue was dissected along the vaginal muscular tube such that the vaginal wall was visible for inspection. The three treatment regions were clearly visible by visual inspection.

The acoustic power delivered to each of the treatment locations is tabulated in Table 2. The duration of each power was varied to observe the effects on peak temperature and applied thermal dose. The peak temperature and peak cumulative dose of 72° C. and $9.1 \times 10^9$ EQmins was observed for the Treatment 2, which showed largest treated region and maximum tissue damage out of the three treatments. The correlation between the dissected tissue images and thermometry recorded by the thermocouples were in good agreement.

TABLE 2

Excised pig GU tract on the tissue holder after treatment.

| EXP | LOCATION | ACOUSTIC POWER (Watts) | DURATION (min:sec) | PEAK TEMP (° C.) | CUMM DOSE (mins) |
|---|---|---|---|---|---|
| Treatment 1 | Near bladder neck | 3-3-3 | 0:38 | 40 | 0 |
| | | 6-6-6 | 1:53 | 65 | $5.6 \times 10^1$ |
| Treatment 2 | Intermediate | 3-3-3 | 0:35 | 42 | 0 |
| | | 6-6-6 | 0:34 | 64 | $1.2 \times 10^1$ |
| | | 6-6-6 | 0:50 | 72 | $9.1 \times 10^1:1$ |
| Treatment 3 | Near urethra opening | 3-3-5 | 2:00 | 57 | $2.4 \times 10^0$ | b. In Vivo Animal Model Studies

Further in vivo animal studies were completed. For purposes of testing the described devices ability to treat SIU, pigs were initially utilized for testing and more accurate SUI testing was done using the ewe due to its closer anatomy with regard to urethra length compared to humans.

i. Pigs Used for Initial In Vivo Animal Model for Device Evaluation and Applicator Design Feedback In viva experiments were conducted to treat SUI using porcine as the animal model. A total of 6 pigs were used for the study. The experimental protocol used for all the experiments is as follows:

1. Anesthetize the pig
2. Insert Transvaginal imaging probe to locate and measure the length of the urethra
3. Remove the imaging probe
4. Use the measurement obtained from ultrasound images in Step 2 to mark the catheter accordingly
5. Use a speculum and insert the catheter under illumination
6. Using the speculum carefully place the catheter according to the marking made on the catheter in Step 4; remove speculum
7. Confirm catheter is oriented correctly in rotational angle
8. Once the catheter is placed accurately, deploy the thermal needle for temperature measurement in the treatment zone
9. Start the treatment
   Monitor temperature and dose in the treatment zone
   Adjust the input acoustic power accordingly
10. After the desired temperature and dose is achieved stop the treatment and remove the catheter The animal was anesthetized and bought to the surgery suite on a stretcher and placed on the surgery table. The health condition of the animal was constantly monitored in terms of heart beat and blood pressure until the end of the experiment. The treatment was conducted by a senior veterinarian and the animal health conditions were monitored by two other junior veterinarians. No significant health issues were observed in any of the experiments during the treatment. After conducting the first experiment using a young pig it was realized that the young pigs (that did not gave birth to piglets) did not had a well-developed reproductive and urinary organs. Thus the length and the diameter of the urethra were not comparable to the human anatomy. Thus for the rest of the experiments older pigs were used. The weight of the pigs ranged from 160-200 lbs and was 1-2 years old and gave birth to piglets several times.

The experiments with the pigs helped in evaluating the applicator design and treatment protocol. At the beginning of the in vivo study, the treatment was given to the animal by placing the ultrasound imaging probe in the vagina and the treatment applicator in the urethra. This procedure was followed such that real time ultrasound imaging may provide information about treatment. In this procedure it was observed that the treatment tissue thickness was decreased significantly due to the pressure exerted on the tissue between the vaginal tube and urethra from the ultrasound imaging probe. In this setup thermocouple sensors were embedded on the ultrasound imaging probe to record the temperature rise at the vagina wall during the treatment.

After feedback from the experiment two thermocouple sensors were placed from the applicator itself as shown in FIG. 4. In addition a measurement sensor may be deployed from the catheter wall into the tissue for direct measurement of the thermal dose in a portion of the target zone of treatment for conformation.

Figure 23:
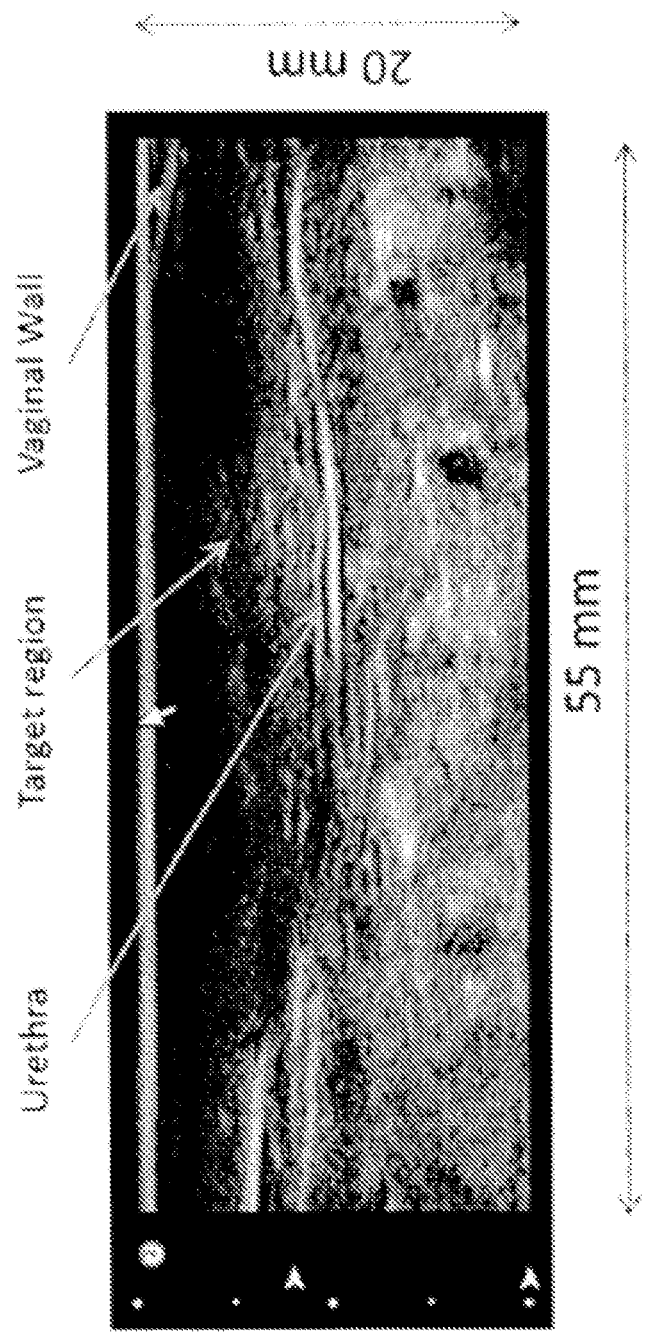
FIG. 23 Ultrasound imaging of the urethra through the vagina wall in pig.

As a result of the pig testing results, the procedure was modified to use the ultrasound imaging probe to estimate the length of the urethra based on the ultrasound images. An ultrasound image of the vagina wall and the urethra by inserting the transurethral ultrasound imaging probe (BPL 9-5/55, Sonix Touch, Ultrasonix, Canada) through the vagina is shown in FIG. 23. The target region for the treatment is indicated in the FIG. 23.

Using the ultrasound images the treatment catheter was marked and inserted into the urethra for treatment. The treatment parameter was controlled using software tools. After each experiment the animal was sacrificed and GU tract was dissected and removed from the animals. First the gross pathology analysis was done followed by fixing the tissue in formalin for further detailed histopathological analysis. The length of the urethra ranged from 12-15 cm.

Figures 24A, 24B, 24C, 24D:
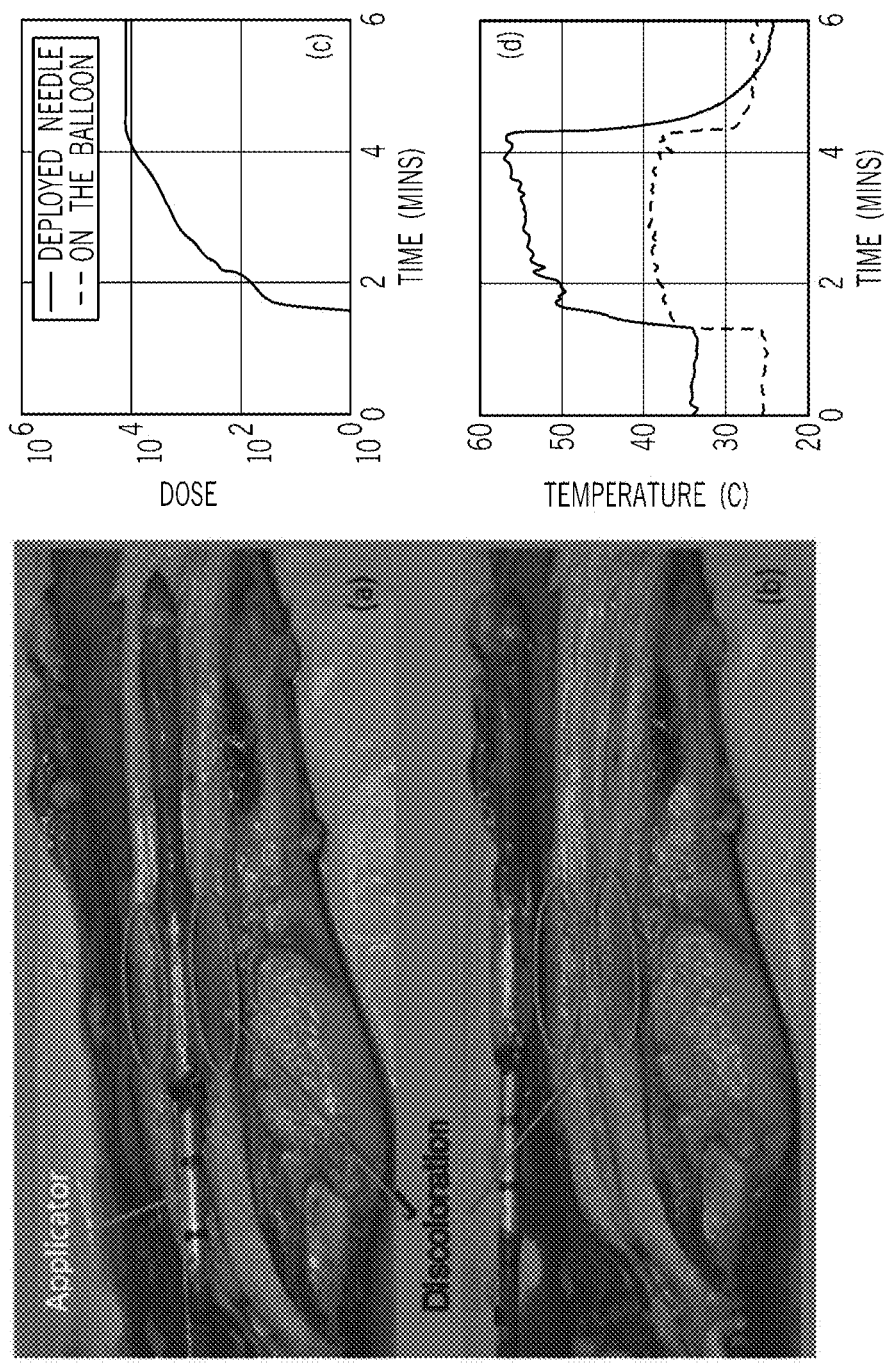
FIGS. 24A-D: (a) Dissected tissue with applicator and discolored tissue due to treatment, (b) another view of the treatment region, (c) the dose delivered as recorded by thermocouples and (d) the temperature profile recorded by the thermocouples.

The tissue was further dissected along the vagina and urethra for analysis. After dissecting the tissue was submerged into triphenyltetrazolium chloride (TTC) for staining. The TTC stajn makes the treated region visually more visible than the normal tissue for easier visual identification of the treatment region. Typically treatment was delivered near the bladder neck, near the urethra opening and intermediate region between the bladder neck and urethra opening. The dissected tissue after treatment is shown in FIGS. 24(a)-(b), where the tissue discoloration in the treatment zone is easily identified. The applicator was placed to verify the treatment location based on the marking on the applicator. Peak temperature and peak dose delivered were 57 C and 12×104 mins of equivalent dose respectively were observed for as shown in FIGS. 24(c) and (d).

Although pigs do not serve as a perfect analog to human pathology, the experiments aided experience with proposed technique and refining the technology in terms of hardware, experimental parameters and software development. The experiment also helped to learn the way the tissues need to be dissected for gross pathology and histological examinations. The experiment also helped to define the range of acoustic power needed to ablate the desired treatment regions as needed.

ii. Ewe as the Animal Model

The length of the urethra in the ewe is within the range of the length of the urethra in human. Hence ewes were used for the purpose of performance evaluation and determination of tissue effects and thermal dose assessment. A total of 6 ewes were used for the study. Out of these 6 ewes, one was a very young ewe used for the first experiment due to the unavailability of the older ewes.

The experimental protocol with minor modifications compared with the protocol used for the pig experiment is as follows:

1. Anesthetize the ewe
2. Insert Transvaginal imaging probe to locate and measure the length of the urethra and check if bladder is empty/full
3. If bladder is full then drain the urine using a drainage catheter
4. Remove the imaging probe
5. Use the measurement obtained from ultrasound images in Step 2 to mark the catheter accordingly
6. Use a speculum and insert the catheter under illumination
7. Using the speculum carefully place the catheter according to the marking made on the catheter in Step 4
8. Confirm catheter is oriented correctly in rotational angle
9. Once the catheter is placed accurately, deploy the thermal sensor needle in target tissue for temperature measurement in the treatment zone
10. Start the treatment
    Monitor temperature and dose in the treatment zone
    Adjust the input acoustic power accordingly
11. After the desired temperature and dose is achieved stop the treatment and remove the catheter
12. Tie tissue using suture at each treatment location to assist pathologist with identification of treatment location for slide preparation The ewe was first anesthetized before the treatment and laid on the surgery table by the stomach keeping the hind limbs hanging from the table. One senior veterinarian along with several personnel was involved to anesthetize the ewe. The condition of the ewe was constantly monitored by two other junior veterinarians during the entire procedure until sacrificing the ewe. During the treatment no significant health problem with respect to pulse rate, blood pressure and bleeding were observed in the ewe in all the experiment. The ewes usually weighed 40-60 Kgs and 3-4 years old. The ewes that had given birth several times were chosen for the study.

A speculum was used to view the urethra opening for visual inspection and help in inserting the catheter easily. Before every treatment the bladder is emptied out using a drainage catheter. A full bladder may stretch the urethra due to weight of the urine in the bladder which results in elongated tissue. To help having relaxed tissue in the GU tract the bladder was emptied before the experiment.

Figure 25:
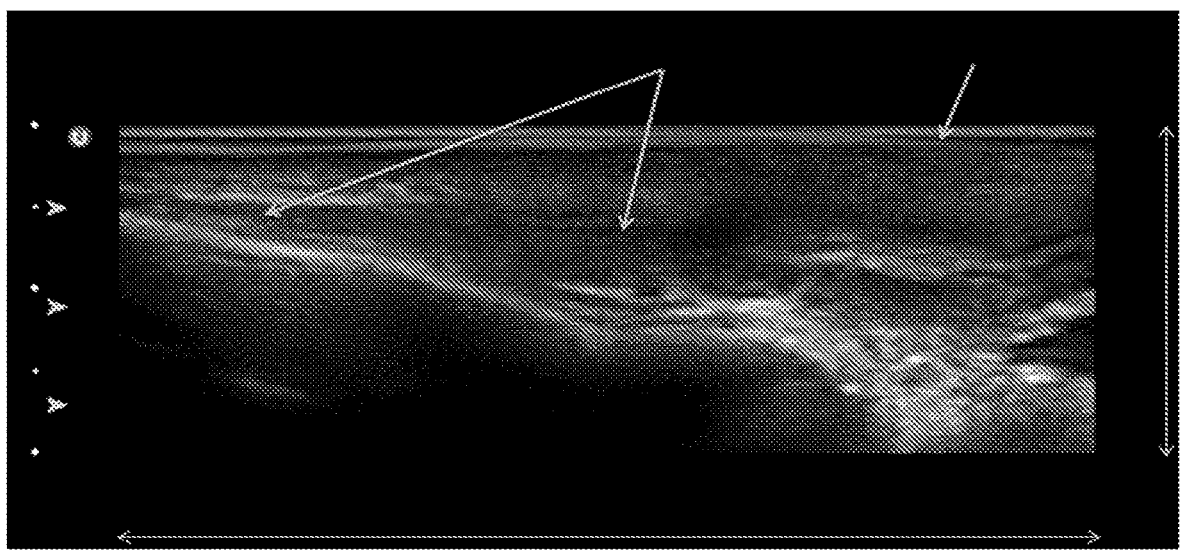
FIG. 25 Ultrasound imaging of the urethra through the vagina wall

The urethra was imaged by inserting a transurethral ultrasound imaging transducer (BPL 9-5/55, Sonix Touch, Ultrasonix, Canada) through the vagina of the ewe. The ultrasound imaging system is an FDA approved system. Ultrasound image of the vaginal wall and the urethra is shown in FIG. 25. The tissue between the vagina wall and the urethra is the treatment region. The ultrasound images helped in measuring the length of the urethra which ranged from 5-7 cm in the ewes.

The treatment catheter was marked based on the ultrasound images. Typically in each experiment tissue near the bladder neck, center of the urethra and near the urethra opening were treated. Single or multiple balloons can be utilized to aid in positioning the transducer along the urethral length relative to the bladder neck.

The treatment is controlled by using software tools. An example screen shot of the treatment screen is shown in FIG. 26, where ultrasound imaging and treatment control can be done simultaneously. The left panel of the treatment screen is dedicated for ultrasound imaging, image contouring, three-dimensional and dose display. Temperature profile of the deployed and balloon thermocouples and it respective doses are shown in the center column of FIG. 26. The doses are shown in terms of equivalent minutes at temperature of 43° C. The bottom right panel controls the RF generator where user can input the required parameters in terms of input frequency and desired output acoustic power. The RF generator panel displays the forward and backward acoustic power to the applicator, delivered acoustic power to the tissue and efficiency of each sector in the applicator. Since each sector were individually controlled allowed to apply different acoustic power to different tissue treatment regions. The top right panel display show several experimental parameters and controls for the water pump and the RF generator. The information such as pump flow rate of 45 mUmin is displayed as shown in FIG. 26. Robust and sophisticated software architecture is used to manage physician, patient and individual treatment information efficient and accurately. This administrative panel can be viewed by selecting the Administrative tab shown at the top of FIG. 26. The software provides very useful and critical information that can help to treat the patient successfully.

Immediately following each experiment, gross pathology analysis were done. The veterinary surgeon carefully removed the portion of the GU tract for gross pathology examination. The length of the urethra was approximately 6 cm. After treatment the tissue in the treated region was stiffer than the surrounding tissue. Minor to major discoloration were observed in the treatment regions.

Figure 27:
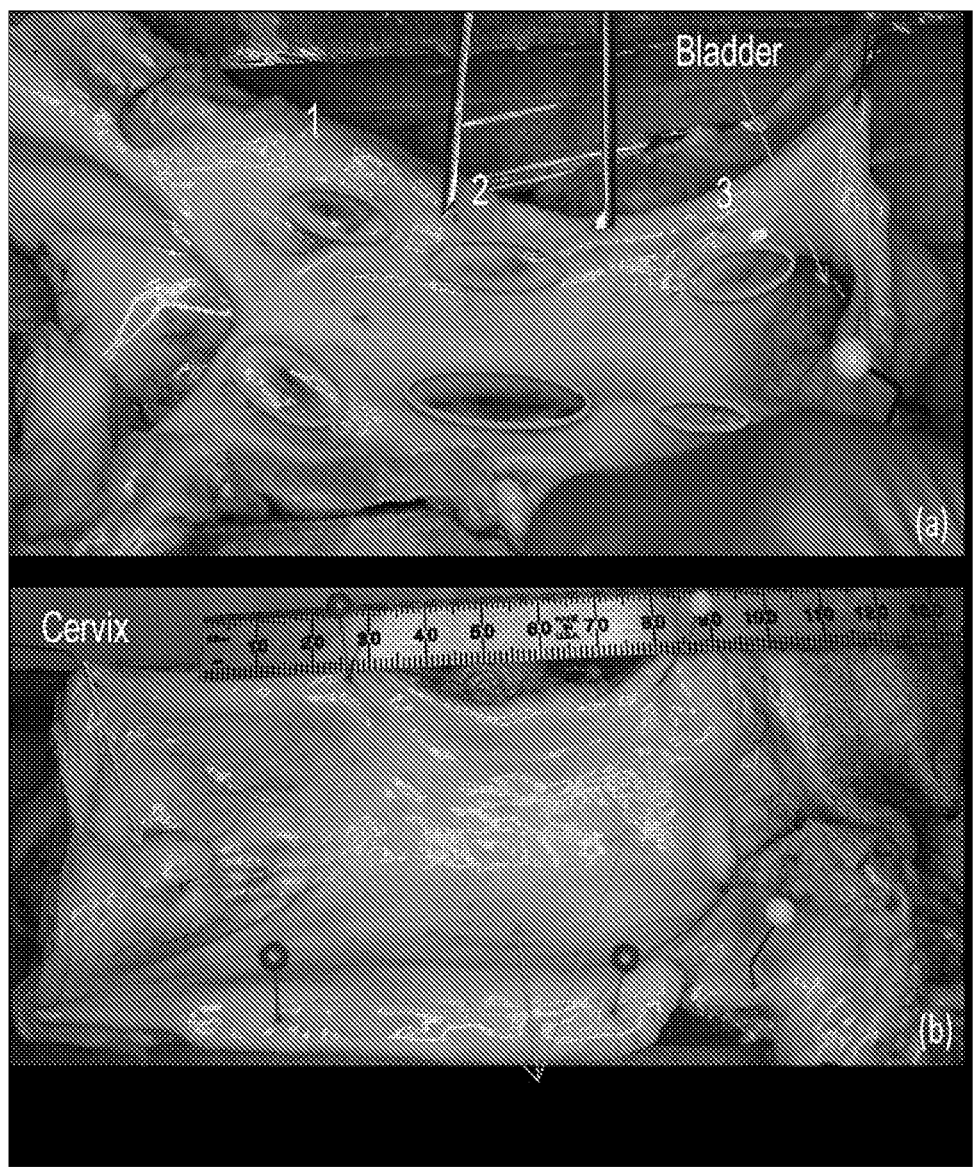
FIGS. 27A-B: Gross pathology of the (a) urethra and (b) vagina wall. The ellipses in (a) indicated the treatment regions 1, 2 and 3.

By dissecting the vagina and urethra, further gross pathological investigation were conducted in each experiment. The top view of the treatment region and the vagina wall are shown in FIGS. 27A-B, respectively. After dissecting, the tissue was submerged into TTC for staining. The three treatment regions specifically near the bladder neck, approximately center of the urethra and near the urethra opening are marked by circle in FIG. 27(a). For shorter urethral lengths, two locations along the urethral length were treated. The darker spot on treatment region 2 was due to insertion of the deployed needle during the treatment to monitor tissue temperature in the treatment region in real time. No damage in the interior of the bladder was observed for all the experiments also shown in FIG. 27(a). The vagina tube was dissected to investigate for any damage on the vagina wall. Similar to bladder interior, no tissue damage regions were observed on the vagina wall as shown in FIG. 27(b).

Figure 28:
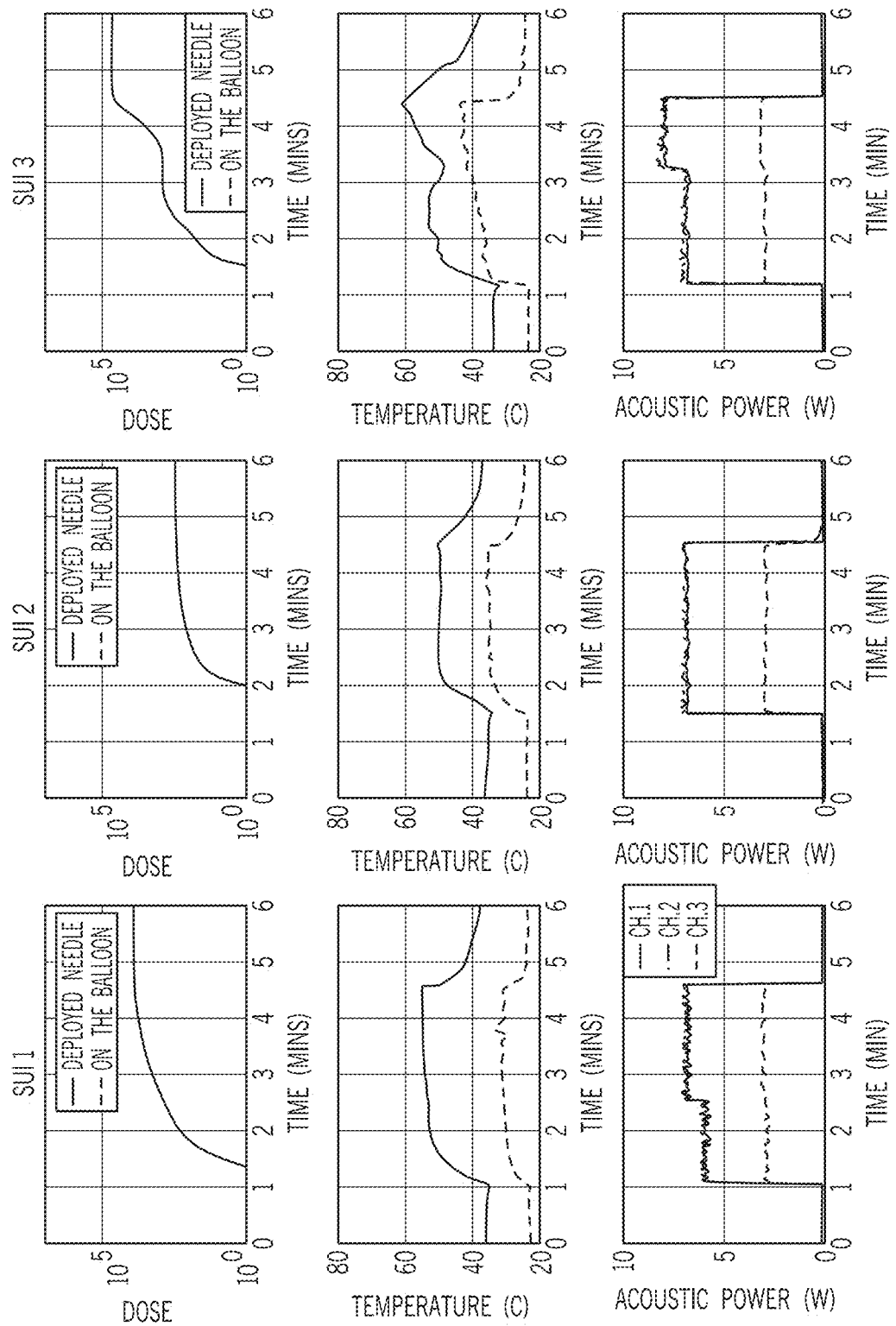
FIG. 28 Thermometry and delivered acoustic power for each of the three treatment regions shown in FIG. 27A-B {5.2.8.} The first, second and third columns (SUI1 SUI2 and SUI3) refers to treatment regions 1, 2 and 3 respectively. Similarly the first, second and third row represents Dose, Temperature and delivered Acoustic Power versus Time graphs respectively.

The thermometry data and the delivered acoustic power on each of the three sectors of the applicator (denoted Ch. 1, 2 and 3) for the gross pathology images shown in FIGS. 27A-B are shown in FIG. 28. The delivered acoustic power for each of the sector and time duration was tabulated in Table 3. All the treatment lasted for 3-3.5 minutes at an average acoustic power of 7, 7 and 3 watts to channels 1, 2 and 3 respectively.

TABLE 3

Experimental parameters used for each treatment region.

| EXP | LOCATION | ACOUSTIC POWER (Watts) | DURA-TION (min:sec) | TOTAL DURATION (min:sec) |
| --- | --- | --- | --- | --- |
| SUI1 | Near bladder neck | 6-6-3<br>7-7-3 | 0:00-1:20<br>1:21-3:30 | 1:20<br>2:09 |
| SUI2 | Intermediate | 7-7-3 | 0:00-3:02 | 3:02 |
| SUI3 | Near urethra opening | 7-7-3<br>8-8-3 | 0:00-2:00<br>2:01-3:17 | 2:00<br>1:17 |

Histology pathology analysis was performed on a subset of specimens after the experiment The treatment region were first cut into thin slices of 1-2 mm thickness and submerged into formalin. Generally three to four histopathology slides were made from each treatment zone. Tissue sections were stained with hematoxylin and eosin (H&E). This staining process involves the application of hematoxylin which colors the nuclei blue and the rest of the structure such as cytoplasm, blood cells is stained at different shades of red and pink. For example blood cells are colored as red in the histology slides. The microscopic slides were examined by pathologists.

iii. Ewe as a Survival Study Animal Model

Initial survival study was conducted on two old ewes that had given birth to lambs several times before the start of the experiment. Both the ewes weighted 66 Kgs approximately. The experimental protocol with minor modifications compared with the previous ewe experiments is as follows:
1. Anesthetize the ewe
2. Insert Transvaginal imaging probe to locate and measure the length of the urethra and check if bladder is empty/full
3. If bladder is full then drain the urine using a drainage catheter
4. Remove the imaging probe
5. Use the measurement obtained from ultrasound images in Step 2 to mark the catheter accordingly
6. Use a speculum and insert the catheter under illumination
7. Using the speculum carefully place the catheter according to the marking made on the catheter in Step 4
8. Confirm catheter is oriented correctly in rotational angle
9. Once the catheter is placed accurately, deploy the thermal sensor needle in target tissue for temperature measurement in the treatment zone
10. Start the treatment
    Monitor temperature and dose in the treatment zone
    Adjust the input acoustic power accordingly
11. After the desired temperature and dose is achieved stop the treatment and remove the catheter
12. Transfer the ewe to the recovery room and monitor the animal for any bleeding. It is a good sign if the animal urinates within 1-2 hours after the recovery.
13. Monitor the animal status for the next 4-5 weeks before sacrifice
14. At necropsy, examine gross pathology tissue changes and prepare samples for histology Specifically Steps 12-14 in the above protocol were different compared to the previous protocol used for the non-survival ewe experiments. The animal preparation and treatment procedure were identical to the non-survival ewe experiment as described above. Two treatment locations were assigned for each of the two ewes. An example of the temperature profile, dose and delivered acoustic power are shown in FIGS. 29A-C. Both treatment for the first ewe demonstrated desired thermal dose ($10^4$-$10^5$ DEQ mins) and peak temperature rise of 55-60° C. For the second ewe both the treatments showed significant thermal dose and temperature profile. The transducer position in the second treatment location of the EWE-200 exhibited much higher temperature/dose in shorter time in target tissue zone outside of urethra; however, note that urethral temperature did not exceed 37° C. Higher target temperature most likely due to reduced blood flow in treated tissue region at that position in urethra.

Both the ewes were frequently monitored for 24 hours after treatment and did not show any urethral bleeding or stricture. The ewes urinated as normal within an hour following the treatment. A series of histopathologic studies of the treated tissues were performed and the slides revealed that the target regions received thermal dose sufficient to cause changes in collagen structure and tissue viability. Non-targeted regions were not affected.

c. Discussion

Figure 30C:
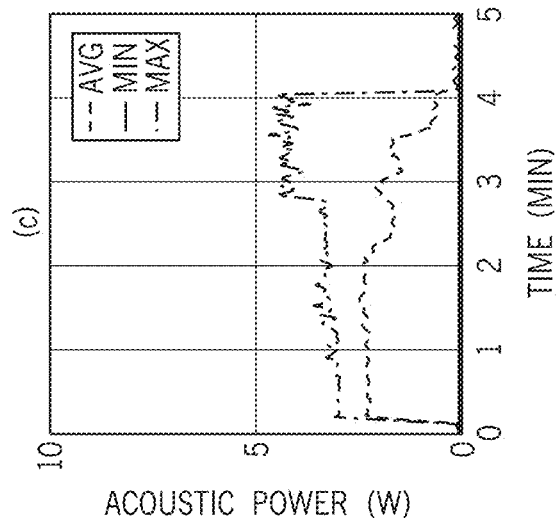
FIGS. 30A-C The average, minimum and maximum applied acoustic power settings used for (a) Channel 1, (b) Channel 2 and (c) Channel 3 in all the ewe experiments.
Figure 30B:
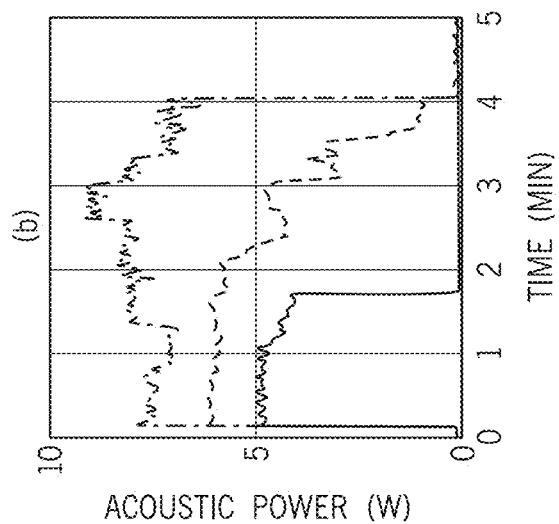
Figure 30A:
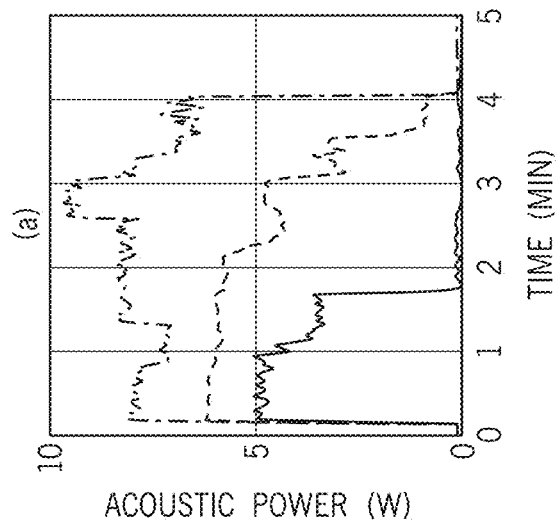

Various levels of applied acoustic power were used to conduct a parametric study to determine the optimal acoustic power needed to rise the tissue temperature to 50-60° C. which is the desired temperature for the treatment. A thermal dose of greater than 240 equivalent minutes at 43° C. triggers the cells initiate the denaturing process in the collagen. A thermal dose of $10^5$-$10^6$ equivalent minutes at 43° C. was the main goal for the treatment. Considering all the 14 experiments performed in ewes, the mean, maximum and minimum acoustic power delivered to the tissue from Channels 1, 2 and 3 are shown in FIGS. 30A-30C. Mean acoustic power levels of 7 W, 7 W and 3 W were delivered to the tissue by Channels 1, 2 and 3 respectively. It has been observed that this mean acoustic power settings showed good treatment region in gross pathological examination with stiffer tissue in the treated region compared to the untreated surrounding tissue.

Figure 31A:
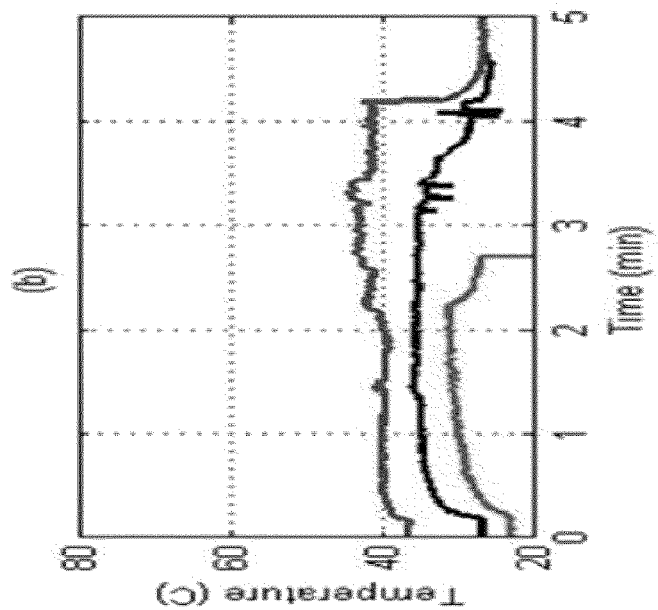
FIGS. 31A-B The average, minimum and maximum temperature recorded by the (a) deployed thermocouple, and (b) thermocouple on the balloon. (The black, red and blue refers to average, minimum and maximum values respectively)
Figure 31B:
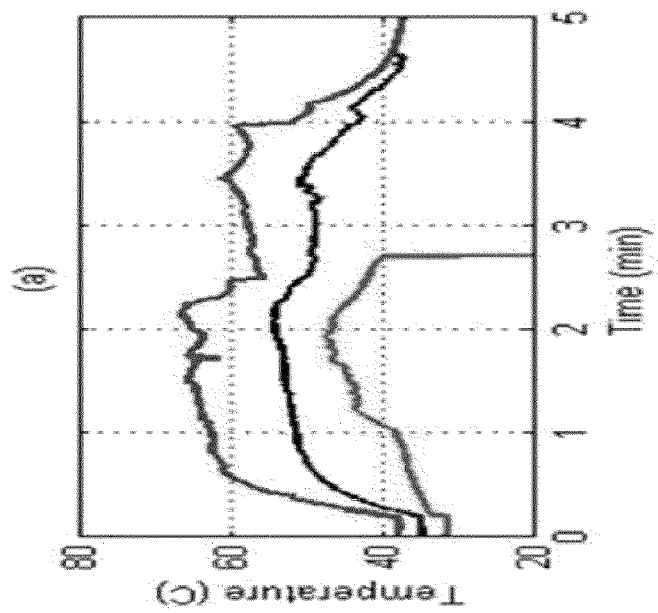

The mean, maximum and minimum temperature and dose recorded by the deployed thermocouple and thermocouple on the balloon are shown in FIGS. 31A-B respectively. The mean temperature recorded by the deployed thermocouple ranges were from 56-58° C. as shown in FIG. 31(a), which was the desired temperature rise required to trigger denaturing the collagen fibrils. Mean temperature of approximately 38-40° C. was recorded by the thermocouple on the balloon during the treatment as shown in FIG. 31.(b). The mean, maximum and minimum dose recorded by the deployed range falls within the desired range of $10^5$-$10^6$ equivalent minutes of 43° C. as shown in FIG. 31(b). Since the temperature recorded by the thermocouple on the balloon was less than 43° C., no dose were recorded for all the experiments as shown in the FIG. 31(b). Two representative experimental results and delivered acoustic power and exposure durations are tabulated in Table 4.

TABLE 4

Experimental parameters and analysis for all ewe experiments.

| EXP | LOCATION | POWER (Watts) | DURATION (min:sec) | PEAK TEMP (C.) | CUMM DOSE (mins) |
|---|---|---|---|---|---|
| EXP DATE: Oct. 10, 2012 | | | | | |
| SU11 | Near bladder neck | 6-6-3 | 1:20 | 53 | $4.90 \times 10<$ |
|  |  | 7-7-3 | 2:09 | 55 | $7.16 \times 10$;j |
| SUI2 | Intermediate | 7-7-3 | 3:02 | 50 | $2.77 \times 10$ |
| SUI3 | Near urethra opening | 7-7-3 | 2:00 | 53 | $7.40 \times 10<$ |
|  |  | 8-8-3 | 1:17 | 61 | $4.65 \times 10^4$ |
| EXP DATE: Oct. 3, 2012 | | | | | |
| SUI1 | Near bladder neck | 5-5-2 | 1:07 | 44 | 0.4 |
|  |  | 6-6-3 | 2:28 | 56 | $2.57 \times 10^3$ |
| SUI2 | Intermediate 1 | 6-6-3 | 3:30 | 57 | $3.80 \times 10^3$ |
| SUI3 | Intermediate 2 | 7-7-3 | 2:40 | 54 | $9.93 \times 10^2$ |
|  |  | 7-7-4 | 1:21 | 59 | $1.71 \times 10^4$ |
| SUI4 | Near urethra opening | 8-8-3 | 0:40 | 58 | $1.46 \times 10^4$ |
|  |  | 7-7-3 | 0:32 | 57 | $2.40 \times 10^4$ |
|  |  | 8-8-3 | 1:18 | 57 | $4.68 \times 10^4$ |
|  |  | 9-9-3 | 0:30 | 59 | $5.76 \times 10^4$ | d. Animal Model Studies Summary

Following the results of the animal study, the optimal treatment parameter ranges for acoustic power, time, maximum temperature, and thermal dose determined based upon a total of 14 Ewe treatment cases were determined for one embodiment.

Multi Balloon Catheter Device

Devices and methods described herein provides the ability to direct energy radially in any desired direction, or in multiple controlled directions around a catheter or similar insertion device 200 to produce a conformal shaped delivery of energy for the purpose of thermal treatment. The device 200 uses a lightly focused or directional ultrasound transducer or multi-sectored tubular (or array of transducers) to heat the tissue to a prescribed temperature, at a prescribed depth, for a prescribed time and access the targeted section of anatomy via a transurethral applicator.

Application of ultrasound energy from within the urethra to target tissue regions can be used to generate tissue remodeling, stiffness changes, or desired tissue changes to treat SUI. The application of heat can be modulated or controlled in temperature and duration for desired physiological effect. For certain implementations, the object of treatment is to apply ultrasound energy to the specific treatment region most impacting for treating a disorder or diseases. Multisectored tubular arrays 230 can be used to treat regions simultaneously.

In one implementation, different treatments being able to position the active transducer 230 or arrays of transducers 230 at a particular position within the length of the treatment area, such as the urethra. This is true for targeting of specific regions within the prostate along the base-to-apex length of the prostate. This is particularly needed for treating stress urinary incontinence in women, where the greatest effect on the collagen and muscular structures affecting SUI are around the central region of the urethra. These represent the urethral distance in the 25% to 75% region of total length. In one implementation, the device 200 is a multi-sectored ultrasonic device 3200 that includes a multi-chambered balloon 3260 for positioning the catheter 210. The multi-chambered balloon 3260 allows for the device 3200 to fix or anchor in relation to an object, such as along the urethra and using the bladder as a means for effectively fixing or anchoring the position of the catheter. The use of multiple chambers 3261 or lumens in the bladder balloon will change the relative position of the ultrasound transducers within, for example, the urethra longitudinally.

Figure 32:
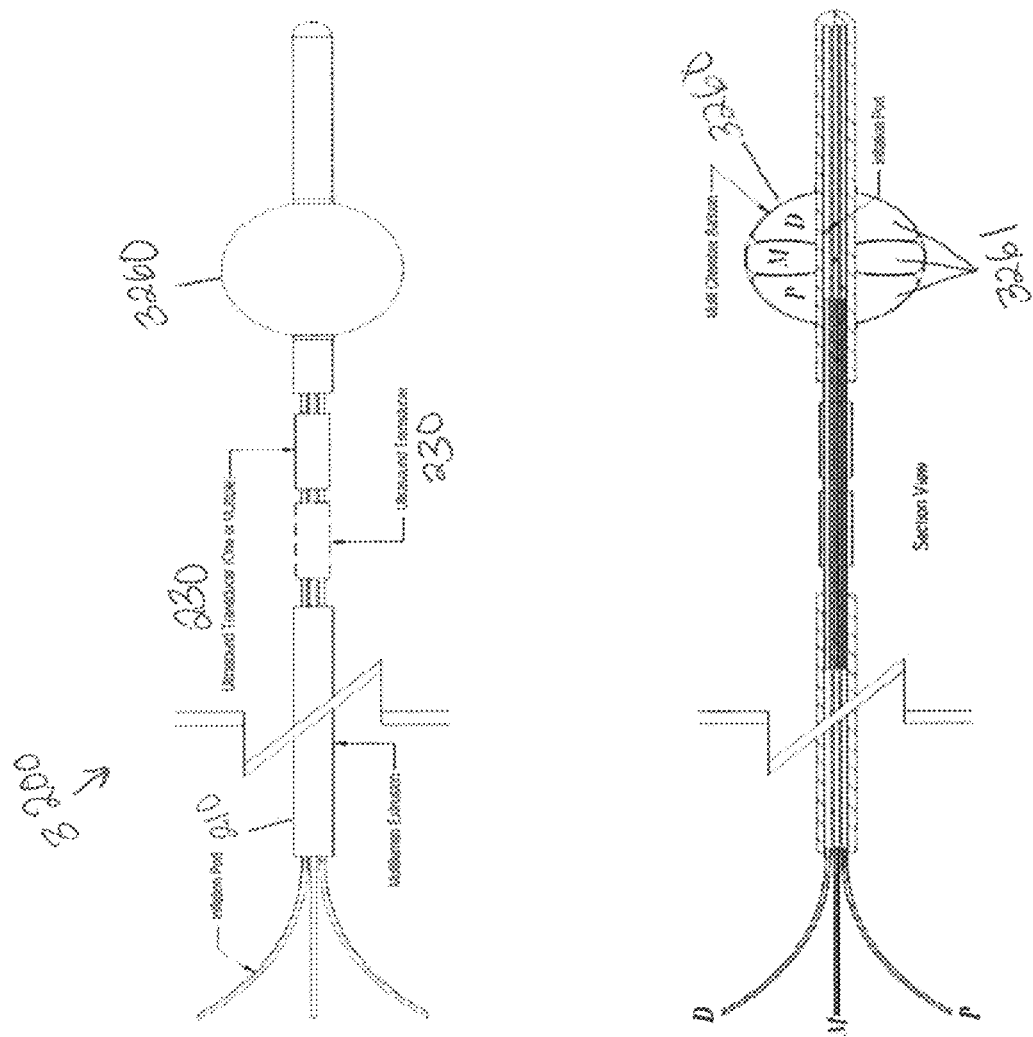
FIG. 32 is a sketch of a two-chambered balloon and a three chambered balloon. Also included is a measurement catheter and bladder balloon with markings which can be color coded based upon distance. This catheter can be used to measure the length of the urethra if needed.

In one implementation, illustrated in FIG. 32, the multi-sectored ultrasonic device 3200 includes the multi-chambered balloon 3260. The device 3200 has a catheter body 210 (in FIGS. 32-34). The device may be similar to show in FIG. 1A and described above as device 200. A cooling mechanism 220 may be provided. One or more transducers 230 are disposed about the catheter body 210. The one or more transducers 230 may be multi-sectored. In one embodiment each sector 240 can be separately powered, such as by a separate wire back to a common power source. In one embodiment, the one or more transducers may be sectored into zones longitudinally instead of or in addition to radially.

Figure 35:
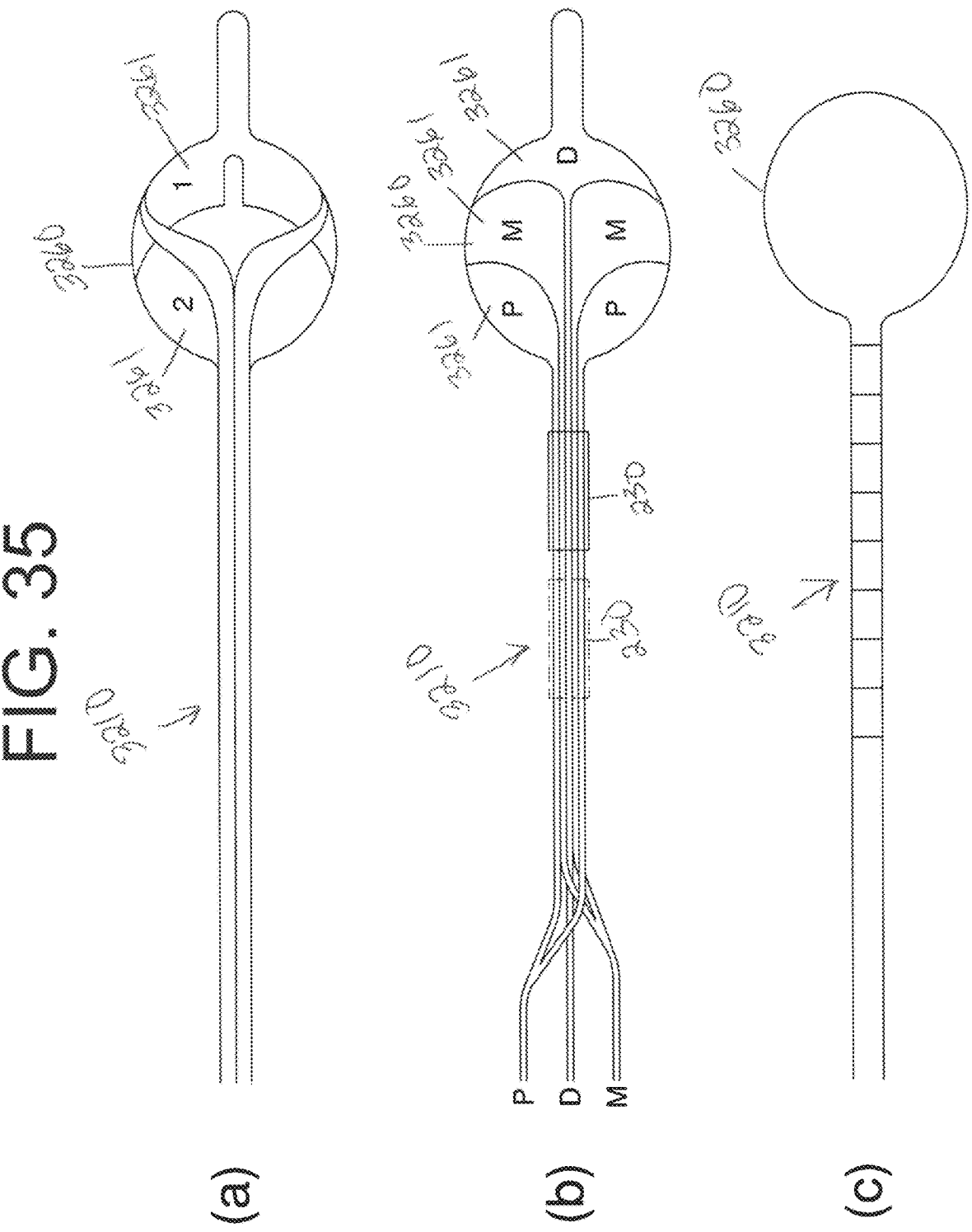
FIG. 35(a) and FIG. 35(b) illustrate a two-chambered balloon and three-chambered balloon, respectively. Also illustrated in FIGS. 35(a)-35(c) is a measurement catheter and bladder balloon with markings which can be color coded based upon distance.

FIG. 35 is a sketch of a balloon 3260 with FIG. 35A illustrating a two-chambered balloon and FIG. 35B illustrating a three chambered balloon. The balloon 3260 may have a plurality of chambers 3261. It will be appreciated that the size, shape, and number of chambers 3261 will determine the ability to position the transducers 230. In an alternative design, each chamber 3261 may comprise a separate balloon rather than each chamber 3261 being part of a unitary structure. In combination with the balloon 3260, a measurement catheter 3210 and visual indicia on the balloon 3260 may be utilized. For example, each chamber 3261 of the multi-chambered balloon 3260 may have a corresponding different color.

Figure 33:
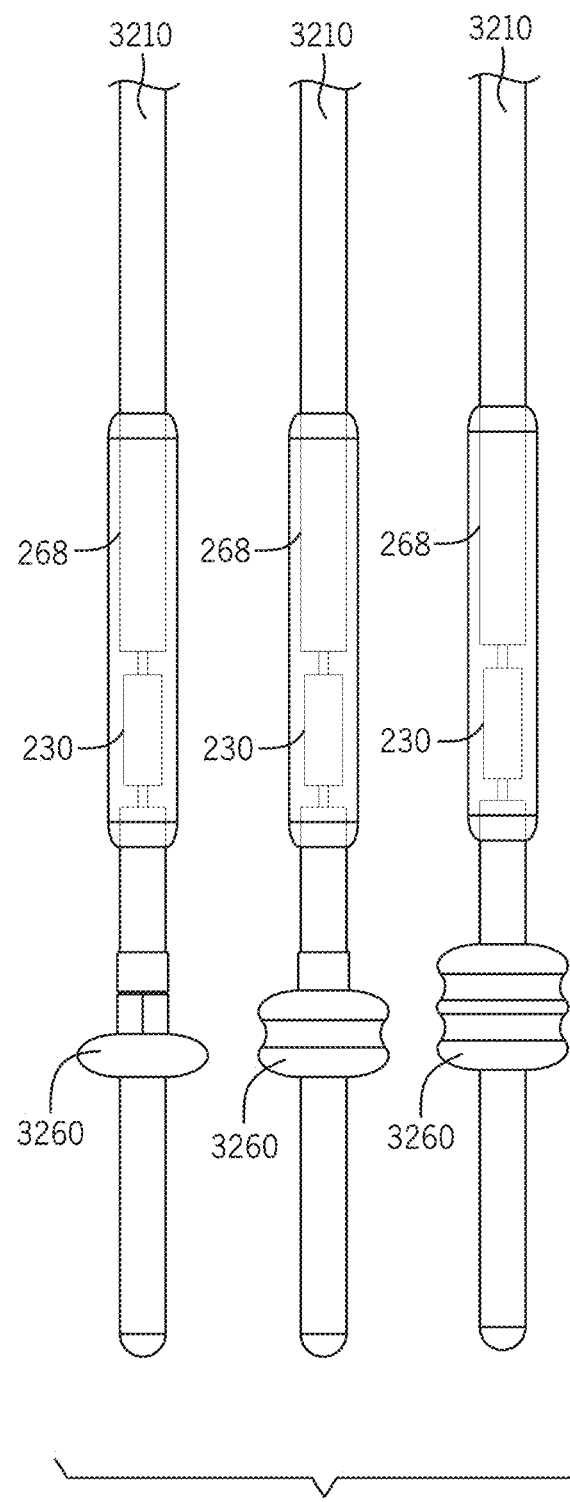
FIG. 33 shows three longitudinal views of a treatment catheter with three different balloons used for positioning the overall catheter within the urethra at the proper position along the length. The same three chambered balloon assembly is shown in perspective view in FIG. 4. The transducer with acoustic coupling balloon is also shown in FIGS. 3 and 4. While these figures are representative, they are in no manner limiting to the various specific configurations of balloons or number of balloons. By inflating a combination of different balloons in the balloon chamber, the distance between the bladder neck and transducer position can be easily varied as shown in FIG. 5. Such innovation will help in using the same catheter design for treating variable urethral lengths.

FIG. 33 shows three longitudinal views of a treatment catheter 3210 with three different balloons 3260 used for positioning the overall catheter 3210 within the urethra at the proper position along the length. The same three chambered balloon 3260 is shown in perspective view in FIG. 34. The transducer 230 with acoustic coupling balloon 268 is also shown FIG. 34. While these figures are representative, they are in no manner limiting to the various specific configurations of balloons or number of balloons. By inflating a combination of different chambers 3261 in the balloon 3260, the distance between the bladder neck and transducer position can be easily varied as shown in FIG. 5. Such innovation will help in using the same catheter design for treating variable urethral lengths or otherwise in positioning the transducers 230.

In one implementation, each chamber 3261 of the balloon 3260 may be divided into two or more sub-chambers (not shown) such that each sub-chamber can be inflated independently. The device 3200 may be positioned within a location in three dimensions by utilizing various levels of inflation each sub-chamber.

Figure 34:
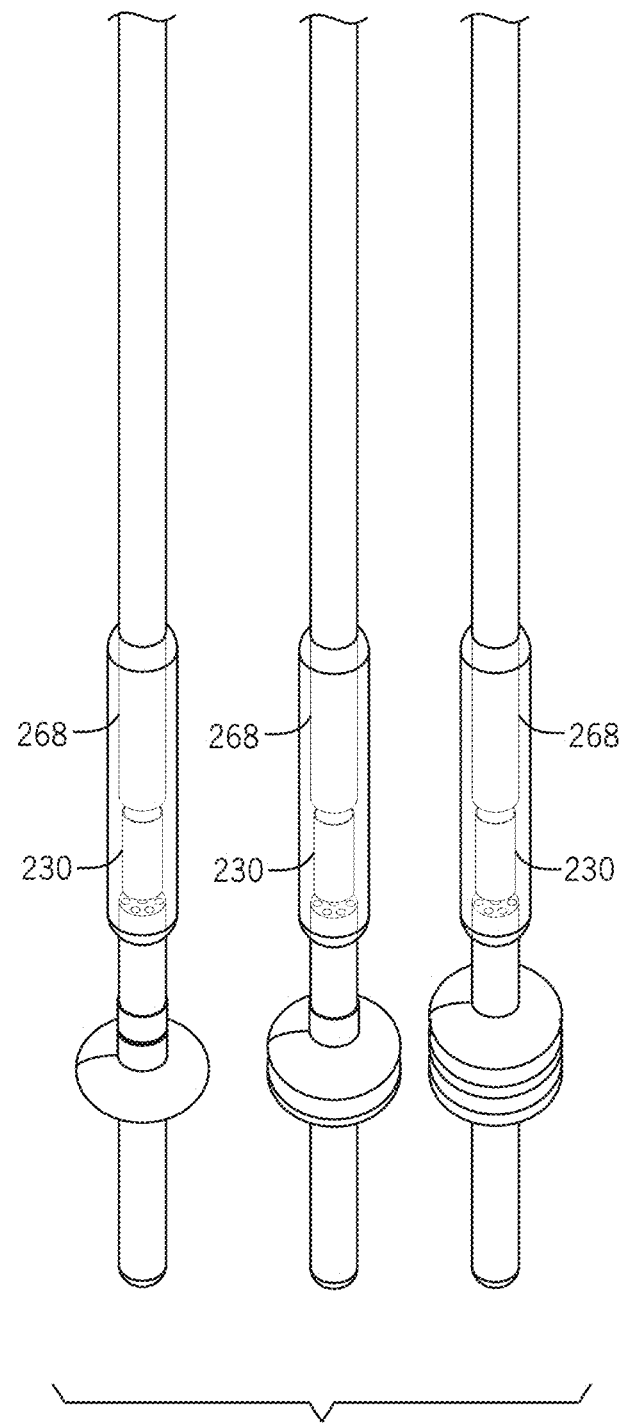
FIG. 34. Longitudinal views of multi-chambered bladder balloon for positioning of treatment transducer or transducers in the proper position along length of urethra.

In another implementation, the multi-chambered balloon 3260 is positioned proximate the transducers 230 rather than distal as shown in FIGS. 32-34. Thus, the distance from the proximate end of the device 3200 to the transducers 230 can be used to control the position of the transducers 230 for treatment in some implementations.

In another implementation, a second multi-chambered balloon 3260 is provided. The second multi-chambered balloon 3260 is positioned opposite the first multi-chambered balloon 3260 with the transducer 230 disposed therebetween. The first and second multi-chambered balloons 3260 may be used in conjunction to secure the catheter 3200 with respect to the treatment subject.

In one implementation, heat a partial annular ring of tissue below the bladder neck along the urethra at a radial distance of 3-10 mm to a temperature above 50° C. and below 75° C. for an appropriate number of seconds to produce collagen shortening and injury sufficient to stimulate healing response. The peak temperature could be approximately 3-5 mm from the urethra surface. The diameter of the partial annular ring of heat (greater than 50° C.) should be 10 mm to about 30 mm maximum. The urethra surface temperature can be regulated to be less than 45° C.

For treatment of benign prostatic hyperplasia (BPH) the energy can be directed specifically to the anterior lateral regions of the prostate at penetrations of 10-35 mm, without damaging the urethra because of separate control of the urethral temperature. The anterior lateral regions include the transition zone which is the most common site of origin of BPH. For treatment of prostate cancer, the energy can be directed to the posterior lateral regions of the gland, which is the most common prostatic site of origin for early stage prostate cancer, or energy can be directed 360 degrees either by producing that pattern radially directly from tubular transducers or by using directive transducer or focused transducers and rotating those to create desired zones of treatment within the prostate.

The urethra surface temperature can be monitored with a thermocouple to regulate applied power/coolant flow to regulate. The applicator diameter can be 2-4 mm in diameter. The balloon 3260 can be 4-10 mm diameter.

In one implementation, ultrasound or acoustic energy can be controlled to produce heat therapy or for acoustic effects alone, or for targeted release of biologic agents or chemical agents, such as targeted microbubbles or nano-carriers, or acoustic or thermal release agents. The synergistic effect of combining ultrasound and microbubbles/biologic agents/nano-carriers will enhance the efficacy of the treatment for cancer treatment.

With respect to the use of substantially any plural and/or singular terms herein, those having skill in the art can translate from the plural to the singular and/or from the singular to the plural as is appropriate to the context and/or application. The various singular/plural permutations may be expressly set forth herein for the sake of clarity.

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed is:

1. An apparatus for ultrasound treatment comprising:
   a catheter;
   at least one multi-sectored transducer in communication with the catheter and comprising a plurality of transducer zones, wherein the at least one multi-sectored transducer produces energy that is electrically subdivided into a plurality of angular transducer energy zones extending radially from the multi-sectored transducer;
   a multi-chambered balloon positioned at a distal end of the catheter at a distal position with respect to the at least one multi-sectored transducer; and
   a cooling system for circulating through the catheter to cool the apparatus and acoustically couple the at least one multi-sectored transducer to a tissue,
   wherein the each of the plurality of transducer zones is independently operable,
   wherein the multi-chambered balloon is configured to anchor the apparatus with respect to a target of the ultrasound treatment, at least a portion of the multi-chambered balloon positionable in a cavity distal to the target of the ultrasound treatment such that the at least one multi-sectored transducer is positioned adjacent to the target of the ultrasound treatment; and
   wherein each chamber of the multi-chambered balloon is coaxially positioned along the longitudinal axis of the catheter, comprises the same shape, is independently inflatable within the cavity to change a longitudinal position of the at least one multi-sectored transducer with respect to the target of the ultrasound treatment and to fix the apparatus at an intersection of a vessel and the cavity.

2. The apparatus of claim 1, wherein the plurality of transducer zones comprise a first transducer zone, a second transducer zone, and a third transducer zone.

3. The apparatus of claim 2, wherein the plurality of transducer zones comprise a first transducer zone, a second transducer zone, a third transducer zone, and a fourth transducer zone.

4. The apparatus of claim 1, wherein the at least one multi-sectored transducer is a tubular transducer.

5. The apparatus of claim 1, further comprising a cooling balloon disposed about the at least one multi-sectored transducer and in communication with the cooling system.

6. The apparatus of claim 1, wherein the multi-chambered balloon comprises a plurality of chambers each having a plurality of sub-chambers, and wherein each sub-chamber is independently inflatable.

7. The apparatus of claim 1, wherein the catheter includes a visual indicia configured to indicate a distance from an end of the catheter.

8. The apparatus of claim 1, wherein the multi-chambered balloon is positioned proximate with respect to the at least one multi-sectored transducer.

9. The apparatus of claim 1, wherein the multi-chambered balloon comprises a two-chambered balloon or a three-chambered balloon.

10. A method for treating tissue comprising:
    inserting a multi-zone ultrasonic catheter to a desired depth relative to the tissue, the multi-zone ultrasonic catheter comprising:
    a catheter;
    at least one multi-sectored transducer in communication with the catheter and comprising a plurality of transducer zones, wherein the at least one multi-sectored transducer produces energy that is electrically subdivided into a plurality of angular transducer energy zones extending radially from the multi-sectored transducer, and each of the transducer zones is independently operable;
    a multi-chambered balloon positioned at a distal end of the catheter at a distal position with respect to the at least one multi-sectored transducer, the multi-chambered balloon being configured to anchor the multi-zone ultrasonic catheter with respect to the tissue, at least a portion of the multi-chambered balloon configured to be positioned in a cavity distal to the tissue such that the at least one multi-sectored transducer is positioned adjacent to the tissue, each chamber of the multi-chambered balloon being coaxially positioned along the longitudinal axis of the catheter and comprising the same shape; and a cooling system for circulating through the catheter to cool the apparatus and acoustically couple the at least one multi-sectored transducer to the tissue;

securing the catheter at the desired depth by selectively and independently inflating one or more chambers of the multi-chambered balloon within the cavity to change the longitudinal position of the at least one multi-sectored transducer with respect to the tissue and to fix the apparatus at an intersection of a vessel and the cavity;

orienting the catheter with respect to a rotational angle;

activating one or more transducer zones of the at least one multi-sectored transducer, wherein activated zones are selected based upon a treatment zone; and monitoring temperature and ultrasound dose in the treatment zone.

11. The method of claim 10, further comprising inserting an imaging probe.

12. The method of claim 11, positioning of the catheter based upon images from the imaging probe.

13. The method of claim 12, monitoring treatment of the tissue based upon images from the imaging probe.

14. The method of claim 10, further comprising deploying a thermal sensor in the tissue to measure temperature in the treatment zone.

15. The method of claim 10, further comprising inflating one or more chambers of a second multi-chamber balloon.

16. The method of claim 10, further comprising deactivating the multi-zone ultrasonic catheter after a desired temperature and dose is achieved.

17. The method of claim 10, wherein the tissue comprises bladder tissue.

18. An apparatus for ultrasound treatment comprising:
a catheter;
at least one transducer in communication with the catheter; and
a multi-chambered balloon positioned at a distal end of the catheter at a distal position with respect to the at least one transducer, wherein:
the multi-chambered balloon is configured to anchor the apparatus with respect to a target of the ultrasound treatment, at least a portion of the multi-chambered balloon positionable in a cavity distal to the target of the ultrasound treatment such that the at least one transducer is positioned adjacent to the target of the ultrasound treatment; and
each chamber of the multi-chambered balloon is coaxially positioned along the longitudinal axis of the catheter, comprises the same shape, and is independently inflatable within the cavity to change a longitudinal position of the at least one transducer with respect to the target of the ultrasound treatment and to fix the apparatus at an intersection of a vessel and the cavity.

19. The apparatus of claim 18, wherein the at least one transducer comprises a multi-sectored transducer having a plurality of transducer zones.

20. The apparatus of claim 18, wherein the at least one transducer comprises an array of transducers having a plurality of transducer zones.

* * * * *